US012569364B2

(12) United States Patent
Johannes et al.

(10) Patent No.: US 12,569,364 B2
(45) Date of Patent: Mar. 10, 2026

(54) FLUID COLLECTION DEVICES, SYSTEMS, AND METHODS

(71) Applicant: PureWick Corporation, El Cajon, CA (US)

(72) Inventors: Ashley Marie Johannes, Atlanta, GA (US); Hollie Trullenque, Houston, TX (US); Megan Evans, Grove City, OH (US); Michelle Root, Malvern, PA (US)

(73) Assignee: PUREWICK CORPORATION, Covington, GA (US)

( * ) Notice: Subject to any disclaimer, the term of this patent is extended or adjusted under 35 U.S.C. 154(b) by 759 days.

(21) Appl. No.: 17/625,941

(22) PCT Filed: Jul. 8, 2020

(86) PCT No.: PCT/US2020/041249
§ 371 (c)(1),
(2) Date: Jan. 10, 2022

(87) PCT Pub. No.: WO2021/007349
PCT Pub. Date: Jan. 14, 2021

(65) Prior Publication Data
US 2022/0241106 A1 Aug. 4, 2022

Related U.S. Application Data

(60) Provisional application No. 62/873,048, filed on Jul. 11, 2019.

(51) Int. Cl.
*A61F 5/451* (2006.01)
*A61L 31/02* (2006.01)
(Continued)

(52) U.S. Cl.
CPC ............ *A61F 5/451* (2013.01); *A61L 31/022* (2013.01); *A61L 31/146* (2013.01); *A61L 31/16* (2013.01); *A61L 2300/406* (2013.01)

(58) Field of Classification Search
CPC .......... A61F 5/451; A61F 5/44; A61L 31/022; A61L 31/146; A61L 31/16; A61L 2300/406
See application file for complete search history.

(56) References Cited

U.S. PATENT DOCUMENTS

| | | |
|---|---|---|
| 737,443 A | 8/1903 | Mooers |
| 1,015,905 A | 1/1912 | Northrop |

(Continued)

FOREIGN PATENT DOCUMENTS

| | | |
|---|---|---|
| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)
(Continued)

*Primary Examiner* — Rebecca E Eisenberg
*Assistant Examiner* — Ted Yang
(74) *Attorney, Agent, or Firm* — Ballard Spahr LLP

(57) ABSTRACT

Examples relate to systems, devices, and methods for removing fluid from a fluid collection device using a vacuum source operably coupled thereto. The fluid collection devices include urine collection devices shaped to complement the female or male anatomy near the respective urethras and the vacuum source is operably coupled to the fluid collection device via one or more sections of conduit. The fluid collection devices include antimicrobial materials in or on one or more components thereof.

8 Claims, 7 Drawing Sheets

(51) Int. Cl.
    *A61L 31/14*         (2006.01)
    *A61L 31/16*         (2006.01)

(56)            References Cited

U.S. PATENT DOCUMENTS

| | | |
|---|---|---|
| 1,032,841 A | 7/1912 | Koenig |
| 1,178,644 A | 4/1916 | Johnson |
| 1,387,726 A | 8/1921 | Karge |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,571,357 A | 10/1951 | Charles |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,175,719 A | 3/1965 | Herndon |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,865,109 A | 2/1975 | Elmore et al. |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,096,897 A | 6/1978 | Cammarata |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,223,677 A | 9/1980 | Anderson |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,403,991 A | 9/1983 | Hill |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A * | 5/1988 | Kuntz ..................... A61F 5/455 |
| | | 4/144.1 |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,784,654 A | 11/1988 | Beecher |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,291 A | 4/1989 | Terauchi et al. |
| 4,820,297 A | 4/1989 | Kaufman et al. |
| 4,841,728 A | 6/1989 | Jean et al. |
| 4,846,818 A | 7/1989 | Keldahl et al. |
| 4,846,819 A | 7/1989 | Welch |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |

(56) References Cited

U.S. PATENT DOCUMENTS

| | | | |
|---|---|---|---|
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-Ho |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,950,262 A | 8/1990 | Takagi |
| 4,955,922 A | 9/1990 | Terauchi |
| 4,957,487 A | 9/1990 | Gerow |
| 4,965,460 A | 10/1990 | Tanaka et al. |
| 4,986,823 A | 1/1991 | Anderson et al. |
| 4,987,849 A | 1/1991 | Sherman |
| 5,002,541 A | 3/1991 | Conkling et al. |
| 5,004,463 A | 4/1991 | Nigay |
| 5,013,308 A | 5/1991 | Sullivan et al. |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,057,092 A | 10/1991 | Webster |
| 5,058,088 A | 10/1991 | Haas et al. |
| 5,071,347 A | 12/1991 | Mcguire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,203,699 A | 4/1993 | Mcguire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,282,795 A | 2/1994 | Finney |
| 5,294,983 A | 3/1994 | Ersoz et al. |
| 5,295,979 A * | 3/1994 | DeLaurentis ..... A61M 25/0017 |
| | | 604/328 |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,459 A | 7/1994 | Lavon et al. |
| 5,340,840 A | 8/1994 | Park et al. |
| 5,382,244 A | 1/1995 | Telang |
| 5,409,014 A | 4/1995 | Napoli et al. |
| 5,409,475 A | 4/1995 | Steer |
| 5,411,495 A | 5/1995 | Willingham |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,593,389 A | 1/1997 | Chang |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,700,254 A | 12/1997 | Mcdowall et al. |
| 5,701,612 A | 12/1997 | Daneshvar |
| 5,705,777 A | 1/1998 | Flanigan et al. |
| 5,735,835 A | 4/1998 | Holland |
| 5,752,944 A | 5/1998 | Dann et al. |
| 5,763,333 A | 6/1998 | Suzuki et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,876,393 A | 3/1999 | Ahr et al. |
| 5,887,291 A | 3/1999 | Bellizzi |
| 5,891,125 A | 4/1999 | Plumley |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,007,526 A | 12/1999 | Passalaqua et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,296,627 B1 | 10/2001 | Edwards |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,415,888 B2 | 7/2002 | An et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,446,454 B1 | 9/2002 | Lee et al. |
| 6,467,570 B1 | 10/2002 | Herold |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,540,729 B1 | 4/2003 | Wada et al. |
| 6,547,771 B2 | 4/2003 | Robertson et al. |
| 6,551,293 B1 | 4/2003 | Mitchell |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,037 B1 | 10/2003 | Bennett |
| 6,635,038 B2 | 10/2003 | Scovel |
| 6,652,495 B1 | 11/2003 | Walker |
| 6,666,850 B1 | 12/2003 | Ahr et al. |

(56) References Cited

U.S. PATENT DOCUMENTS

| | | | |
|---|---|---|---|
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,166,092 B2 | 1/2007 | Elson et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,658,730 B2 | 2/2010 | Conley |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,587 B1 | 3/2013 | Gmuer et al. |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |

(56) References Cited

U.S. PATENT DOCUMENTS

| | | | |
|---|---|---|---|
| 9,187,220 B2 | 11/2015 | Biesecker et al. | |
| 9,199,772 B2 | 12/2015 | Krippendorf | |
| 9,233,020 B2 | 1/2016 | Matsumiya | |
| 9,248,058 B2 | 2/2016 | Conway et al. | |
| 9,308,118 B1 | 4/2016 | Dupree et al. | |
| 9,309,029 B2 | 4/2016 | Incorvia et al. | |
| 9,333,281 B2 | 5/2016 | Giezendanner et al. | |
| 9,381,108 B2 | 7/2016 | Longoni et al. | |
| 9,382,047 B2 | 7/2016 | Schmidtner et al. | |
| 9,402,424 B2 | 8/2016 | Roy | |
| 9,456,937 B2 | 10/2016 | Ellis | |
| 9,480,595 B2 | 11/2016 | Baham et al. | |
| 9,517,865 B2 | 12/2016 | Albers et al. | |
| D777,941 S | 1/2017 | Piramoon | |
| 9,533,806 B2 | 1/2017 | Ding et al. | |
| 9,550,611 B2 | 1/2017 | Hodge | |
| 9,555,930 B2 | 1/2017 | Campbell et al. | |
| 9,623,159 B2 | 4/2017 | Locke | |
| D789,522 S | 6/2017 | Burgess et al. | |
| 9,687,849 B2 | 6/2017 | Bruno et al. | |
| 9,694,949 B2 | 7/2017 | Hendricks et al. | |
| 9,709,048 B2 | 7/2017 | Kinjo | |
| 9,713,547 B2 | 7/2017 | Lee et al. | |
| 9,732,754 B2 | 8/2017 | Huang et al. | |
| 9,752,564 B2 | 9/2017 | Arceno et al. | |
| 9,788,992 B2 | 10/2017 | Harvie | |
| D804,907 S | 12/2017 | Sandoval | |
| 9,868,564 B2 | 1/2018 | Mcgirr et al. | |
| D814,239 S | 4/2018 | Arora | |
| D817,484 S | 5/2018 | Lafond | |
| 10,037,640 B2 | 7/2018 | Gordon | |
| 10,058,470 B2 | 8/2018 | Phillips | |
| 10,098,990 B2 | 10/2018 | Koch et al. | |
| D835,264 S | 12/2018 | Mozzicato et al. | |
| D835,779 S | 12/2018 | Mozzicato et al. | |
| D840,533 S | 2/2019 | Mozzicato et al. | |
| D840,534 S | 2/2019 | Mozzicato et al. | |
| 10,225,376 B2 | 3/2019 | Perez Martinez | |
| 10,226,376 B2* | 3/2019 | Sanchez | A61F 5/443 |
| 10,258,517 B1 | 4/2019 | Maschino et al. | |
| D848,612 S | 5/2019 | Mozzicato et al. | |
| 10,307,305 B1 | 6/2019 | Hodges | |
| 10,335,121 B2 | 7/2019 | Desai | |
| D856,512 S | 8/2019 | Cowart et al. | |
| 10,376,406 B2 | 8/2019 | Newton | |
| 10,376,407 B2 | 8/2019 | Newton | |
| 10,390,989 B2* | 8/2019 | Sanchez | A61F 5/453 |
| D858,144 S | 9/2019 | Fu | |
| 10,406,039 B2 | 9/2019 | Villarreal | |
| 10,407,222 B2 | 9/2019 | Allen | |
| 10,478,356 B2 | 11/2019 | Griffin | |
| 10,500,108 B1 | 12/2019 | Maschino et al. | |
| 10,502,198 B2 | 12/2019 | Stumpf et al. | |
| 10,538,366 B2 | 1/2020 | Pentelovitch et al. | |
| 10,569,938 B2 | 2/2020 | Zhao et al. | |
| 10,577,156 B2 | 3/2020 | Dagnelie et al. | |
| RE47,930 E | 4/2020 | Cho | |
| 10,618,721 B2 | 4/2020 | Vazin | |
| D884,390 S | 5/2020 | Wang | |
| 10,669,079 B2 | 6/2020 | Freedman et al. | |
| D892,315 S | 8/2020 | Airy | |
| 10,730,672 B2 | 8/2020 | Bertram et al. | |
| 10,737,848 B2 | 8/2020 | Philip et al. | |
| 10,765,854 B2 | 9/2020 | Law et al. | |
| 10,766,670 B2 | 9/2020 | Kittmann | |
| 10,799,386 B1 | 10/2020 | Harrison | |
| 10,806,642 B2 | 10/2020 | Tagomori et al. | |
| D901,214 S | 11/2020 | Hu | |
| 10,849,799 B2 | 12/2020 | Nishikawa et al. | |
| 10,857,025 B2 | 12/2020 | Davis et al. | |
| 10,865,017 B1 | 12/2020 | Cowart et al. | |
| 10,889,412 B2 | 1/2021 | West et al. | |
| 10,913,581 B2 | 2/2021 | Stahlecker | |
| D912,244 S | 3/2021 | Rehm et al. | |
| 10,952,889 B2 | 3/2021 | Newton et al. | |
| 10,973,378 B2 | 4/2021 | Ryu et al. | |
| 10,973,678 B2* | 4/2021 | Newton | A61F 5/453 |
| 10,974,874 B2 | 4/2021 | Ragias et al. | |
| 11,000,401 B2 | 5/2021 | Ecklund et al. | |
| D923,365 S | 6/2021 | Wang | |
| 11,026,829 B2 | 6/2021 | Harvie | |
| 11,027,900 B2 | 6/2021 | Liu | |
| 11,045,346 B2 | 6/2021 | Argent et al. | |
| D928,946 S | 8/2021 | Sanchez et al. | |
| 11,090,183 B2 | 8/2021 | Sanchez et al. | |
| 11,160,695 B2 | 11/2021 | Febo et al. | |
| 11,160,697 B2 | 11/2021 | Maschino et al. | |
| 11,168,420 B2 | 11/2021 | Kinugasa et al. | |
| 11,179,506 B2 | 11/2021 | Barr et al. | |
| 11,207,206 B2 | 12/2021 | Sharma et al. | |
| 11,226,376 B2 | 1/2022 | Yamauchi et al. | |
| 11,253,389 B2 | 2/2022 | Sharma et al. | |
| 11,253,407 B2 | 2/2022 | Miao et al. | |
| 11,326,586 B2 | 5/2022 | Milner et al. | |
| 11,369,508 B2 | 6/2022 | Ecklund et al. | |
| 11,369,524 B2 | 6/2022 | Hubbard et al. | |
| 11,376,152 B2 | 7/2022 | Sanchez et al. | |
| 11,382,786 B2 | 7/2022 | Sanchez et al. | |
| 11,382,788 B2 | 7/2022 | Hjorth et al. | |
| 11,389,318 B2 | 7/2022 | Radl et al. | |
| 11,395,871 B2 | 7/2022 | Radl et al. | |
| 11,399,990 B2 | 8/2022 | Suyama | |
| 11,426,303 B2 | 8/2022 | Davis et al. | |
| 11,504,265 B2 | 11/2022 | Godinez et al. | |
| 11,529,252 B2 | 12/2022 | Glithero et al. | |
| 11,547,788 B2 | 1/2023 | Radl et al. | |
| 11,806,266 B2 | 11/2023 | Sanchez et al. | |
| 11,839,567 B2 | 12/2023 | Davis et al. | |
| D1,010,109 S | 1/2024 | Ecklund et al. | |
| 11,857,716 B2 | 1/2024 | Lee et al. | |
| 11,865,030 B2 | 1/2024 | Davis et al. | |
| 11,890,221 B2 | 2/2024 | Ulreich et al. | |
| 11,925,575 B2 | 3/2024 | Newton | |
| 11,938,053 B2 | 3/2024 | Austermann et al. | |
| 11,944,740 B2 | 4/2024 | Hughett et al. | |
| 11,994,122 B2 | 5/2024 | Bodain | |
| 11,998,475 B2 | 6/2024 | Becker et al. | |
| 12,023,457 B2 | 7/2024 | Mann et al. | |
| 12,042,422 B2 | 7/2024 | Davis et al. | |
| D1,038,385 S | 8/2024 | Ecklund et al. | |
| 12,090,083 B2 | 9/2024 | Ecklund et al. | |
| 12,133,813 B2 | 11/2024 | Ulreich et al. | |
| 12,138,195 B2 | 11/2024 | Alder et al. | |
| 2001/0037097 A1 | 11/2001 | Cheng et al. | |
| 2001/0054426 A1 | 12/2001 | Knudson et al. | |
| 2002/0019614 A1 | 2/2002 | Woon | |
| 2002/0026161 A1 | 2/2002 | Grundke | |
| 2002/0026163 A1 | 2/2002 | Grundke | |
| 2002/0087131 A1 | 7/2002 | Wolff et al. | |
| 2002/0091364 A1 | 7/2002 | Prabhakar | |
| 2002/0189992 A1 | 12/2002 | Schmidt et al. | |
| 2002/0193760 A1 | 12/2002 | Thompson | |
| 2002/0193762 A1 | 12/2002 | Suydam | |
| 2003/0004436 A1 | 1/2003 | Schmidt et al. | |
| 2003/0032931 A1 | 2/2003 | Grundke et al. | |
| 2003/0032944 A1 | 2/2003 | Cawood | |
| 2003/0073964 A1 | 4/2003 | Palumbo et al. | |
| 2003/0120178 A1 | 6/2003 | Heki | |
| 2003/0157859 A1 | 8/2003 | Ishikawa | |
| 2003/0181880 A1 | 9/2003 | Schwartz | |
| 2003/0195484 A1 | 10/2003 | Harvie | |
| 2003/0204173 A1 | 10/2003 | Burns et al. | |
| 2003/0233079 A1 | 12/2003 | Parks et al. | |
| 2004/0006321 A1* | 1/2004 | Cheng | A61F 5/453 |
| | | | 604/349 |
| 2004/0015141 A1 | 1/2004 | Cheng et al. | |
| 2004/0056122 A1 | 3/2004 | Male et al. | |
| 2004/0084465 A1 | 5/2004 | Luburic | |
| 2004/0127872 A1 | 7/2004 | Petryk et al. | |
| 2004/0128749 A1 | 7/2004 | Scott | |
| 2004/0143229 A1 | 7/2004 | Easter | |
| 2004/0147863 A1 | 7/2004 | Diaz et al. | |
| 2004/0147894 A1 | 7/2004 | Mizutani et al. | |
| 2004/0158221 A1 | 8/2004 | Mizutani et al. | |

(56)                References Cited

U.S. PATENT DOCUMENTS

| | | |
|---|---|---|
| 2004/0176731 A1 | 9/2004 | Cheng et al. |
| 2004/0176746 A1 | 9/2004 | Forral |
| 2004/0191919 A1 | 9/2004 | Unger et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0197645 A1 | 9/2005 | Karpowicz et al. |
| 2005/0273920 A1 | 12/2005 | Marinas |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0077099 A1 * | 3/2008 | House ..................... A61F 5/453 |
| | | 604/349 |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0226541 A1 * | 9/2009 | Scholz .................... A61P 31/04 |
| | | 424/672 |
| 2009/0234312 A1 | 9/2009 | Otoole et al. |
| 2009/0251510 A1 | 10/2009 | Noro et al. |
| 2009/0259206 A1 | 10/2009 | Kai et al. |
| 2009/0264840 A1 | 10/2009 | Virginio |
| 2009/0270822 A1 | 10/2009 | Medeiros |
| 2009/0281510 A1 | 11/2009 | Fisher |
| 2009/0283982 A1 | 11/2009 | Thomas |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1 * | 5/2012 | Sharma .................. A61M 25/04 |
| | | 604/328 |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |

(56) References Cited

U.S. PATENT DOCUMENTS

| | | |
|---|---|---|
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0165880 A1* | 6/2013 | Amos ..................... A61L 15/20 |
| | | 514/159 |
| 2013/0218112 A1 | 8/2013 | Thompson |
| 2013/0245496 A1* | 9/2013 | Wells ................ A61M 25/0017 |
| | | 600/581 |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1* | 2/2014 | Dunbar ............. A61F 13/15577 |
| | | 604/394 |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0359996 A1* | 12/2015 | Arora ................ A61M 25/0017 |
| | | 600/300 |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1* | 12/2016 | Sanchez .................. A61F 5/453 |
| | | 604/319 |
| 2017/0007438 A1 | 1/2017 | Harvie |
| 2017/0014560 A1 | 1/2017 | Minskoff et al. |
| 2017/0042748 A1 | 2/2017 | Griffin |
| 2017/0100276 A1 | 4/2017 | Joh |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez .................. A61F 5/443 |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1* | 2/2018 | Newton .................. A61M 1/88 |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis ..................... A61F 5/451 |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133126 A1* | 5/2019 | Modak ................... A61L 29/06 |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1* | 6/2020 | Wiygul ............. A61M 25/0017 |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |

(56) References Cited

U.S. PATENT DOCUMENTS

| | | |
|---|---|---|
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0384242 A1* | 12/2020 | Havard ............... A61M 25/007 |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Yin et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |

(56) References Cited

U.S. PATENT DOCUMENTS

| | | | |
|---|---|---|---|
| 2024/0058161 | A1 | 2/2024 | Ulreich et al. |
| 2024/0065881 | A1 | 2/2024 | Kuroda et al. |
| 2024/0099874 | A1 | 3/2024 | Sanchez et al. |
| 2024/0110318 | A1 | 4/2024 | Bendt et al. |
| 2024/0123134 | A1 | 4/2024 | Kharkar et al. |
| 2024/0148539 | A1 | 5/2024 | Austermann et al. |
| 2024/0261131 | A1 | 8/2024 | Garvey et al. |

FOREIGN PATENT DOCUMENTS

| | | | | |
|---|---|---|---|---|
| CA | 2165286 | C | 9/1999 | |
| CA | 2354132 | A1 | 6/2000 | |
| CA | 2359091 | C | 9/2003 | |
| CA | 2488867 | C | 8/2007 | |
| CA | 3050918 | A1 | 8/2018 | |
| CA | 3098571 | A1 | 11/2019 | |
| CN | 2269203 | Y | 12/1997 | |
| CN | 1332620 | A | 1/2002 | |
| CN | 1434693 | A | 8/2003 | |
| CN | 1533755 | A | 10/2004 | |
| CN | 1602825 | A | 4/2005 | |
| CN | 1720888 | A | 1/2006 | |
| CN | 2936204 | Y | 8/2007 | |
| CN | 101262836 | A | 9/2008 | |
| CN | 101522148 | A | 9/2009 | |
| CN | 102159159 | A | 8/2011 | |
| CN | 202184840 | U | 4/2012 | |
| CN | 102481441 | A | 5/2012 | |
| CN | 202463712 | U | 10/2012 | |
| CN | 202950810 | U | 5/2013 | |
| CN | 103533968 | A | 1/2014 | |
| CN | 103717180 | A | 4/2014 | |
| CN | 204562697 | U | 8/2015 | |
| CN | 105411783 | A | 3/2016 | |
| CN | 105451693 | A | 3/2016 | |
| CN | 105534632 | A | 5/2016 | |
| CN | 106132360 | A * | 11/2016 | ....... A61F 13/00038 |
| CN | 205849719 | U | 1/2017 | |
| CN | 205924282 | U | 2/2017 | |
| CN | 106726089 | A | 5/2017 | |
| CN | 107847384 | A | 3/2018 | |
| CN | 107920912 | A | 4/2018 | |
| CN | 108420590 | A | 8/2018 | |
| CN | 209285902 | U | 8/2019 | |
| CN | 110381883 | A | 10/2019 | |
| CN | 211198839 | U | 8/2020 | |
| CN | 111991136 | A | 11/2020 | |
| CN | 112022488 | A | 12/2020 | |
| CN | 212234893 | U | 12/2020 | |
| CN | 212466312 | U | 2/2021 | |
| CN | 112566550 | A | 3/2021 | |
| CN | 112603184 | A | 4/2021 | |
| CN | 213490035 | U | 6/2021 | |
| CN | 114007493 | A | 2/2022 | |
| CN | 114375187 | A | 4/2022 | |
| CN | 116096332 | A | 5/2023 | |
| DE | 79818 | C | 10/1893 | |
| DE | 1516466 | A1 | 6/1969 | |
| DE | 2721330 | A1 | 11/1977 | |
| DE | 2742298 | A1 | 3/1978 | |
| DE | 9407554.9 | U1 | 5/1995 | |
| DE | 4443710 | A1 | 6/1995 | |
| DE | 4416094 | A1 | 11/1995 | |
| DE | 4236097 | C2 | 10/1996 | |
| DE | 19619597 | A1 | 11/1997 | |
| DE | 102005037762 | B3 | 9/2006 | |
| DE | 102011103783 | A1 | 12/2012 | |
| DE | 102012112818 | A1 | 6/2014 | |
| DE | 202015104597 | U1 | 7/2016 | |
| DE | 102020121462 | B3 | 1/2022 | |
| DK | 9600118 | | 11/1996 | |
| EP | 0032138 | A2 | 7/1981 | |
| EP | 0066070 | B1 | 12/1982 | |
| EP | 0068712 | A1 | 1/1983 | |
| EP | 0140470 | A1 | 5/1985 | |
| EP | 0140471 | B1 | 5/1988 | |
| EP | 0274753 | A2 | 7/1988 | |
| EP | 0119143 | B1 | 11/1988 | |
| EP | 0483592 | A1 | 5/1992 | |
| EP | 0610638 | A1 | 8/1994 | |
| EP | 0613355 | A1 | 9/1994 | |
| EP | 0613355 | B1 | 1/1997 | |
| EP | 0787472 | A1 | 8/1997 | |
| EP | 0966936 | A1 | 12/1999 | |
| EP | 0987293 | A1 | 3/2000 | |
| EP | 1063953 | A1 | 1/2001 | |
| EP | 0653928 | B1 | 10/2002 | |
| EP | 1332738 | A1 | 8/2003 | |
| EP | 1382318 | A1 | 1/2004 | |
| EP | 1089684 | B1 | 10/2004 | |
| EP | 1616542 | A1 | 1/2006 | |
| EP | 1382318 | B1 | 5/2006 | |
| EP | 1063953 | B1 | 1/2007 | |
| EP | 1658831 | B1 | 1/2008 | |
| EP | 1872752 | A1 | 1/2008 | |
| EP | 2180907 | A1 | 5/2010 | |
| EP | 2380532 | A1 | 10/2011 | |
| EP | 2389908 | A1 | 11/2011 | |
| EP | 2601916 | A1 | 6/2013 | |
| EP | 2676643 | A1 | 12/2013 | |
| EP | 2997950 | A2 | 3/2016 | |
| EP | 2879534 | B1 | 3/2017 | |
| EP | 3424471 | A1 | 1/2019 | |
| EP | 3169292 | B1 | 11/2019 | |
| EP | 3753492 | A1 | 12/2020 | |
| EP | 3788992 | A1 | 3/2021 | |
| EP | 3576689 | B1 | 3/2022 | |
| EP | 3752110 | B1 | 3/2022 | |
| EP | 3787570 | B1 | 3/2022 | |
| EP | 4025163 | A1 | 7/2022 | |
| EP | 3463180 | B1 | 3/2023 | |
| EP | 3569205 | B1 | 6/2023 | |
| EP | 4382082 | A2 | 6/2024 | |
| EP | 4445881 | A2 | 10/2024 | |
| EP | 4464288 | A2 | 11/2024 | |
| GB | 871820 | A | 7/1961 | |
| GB | 1011517 | A | 12/1965 | |
| GB | 1467144 | A | 3/1977 | |
| GB | 2106395 | A | 4/1983 | |
| GB | 2106784 | A | 4/1983 | |
| GB | 2148126 | A | 5/1985 | |
| GB | 2171315 | A | 8/1986 | |
| GB | 2181953 | A | 5/1987 | |
| GB | 2148126 | B | 7/1987 | |
| GB | 2191095 | A | 12/1987 | |
| GB | 2199750 | A | 7/1988 | |
| GB | 2260907 | A | 5/1993 | |
| GB | 2462267 | A | 2/2010 | |
| GB | 2469496 | A | 10/2010 | |
| GB | 2490327 | A | 10/2012 | |
| GB | 2507318 | A | 4/2014 | |
| GB | 2612752 | A | 5/2023 | |
| IT | 201800009129 | A1 | 4/2020 | |
| JP | S498638 | U | 1/1974 | |
| JP | S5410596 | A | 1/1979 | |
| JP | S5410596 | Y2 | 5/1979 | |
| JP | S54155729 | U | 10/1979 | |
| JP | S55155618 | A | 12/1980 | |
| JP | S56152629 | U | 11/1981 | |
| JP | S57142534 | U | 9/1982 | |
| JP | S5888596 | U | 6/1983 | |
| JP | S58188016 | U | 12/1983 | |
| JP | S63107780 | U | 7/1988 | |
| JP | H0267530 | A | 3/1990 | |
| JP | H02103871 | A | 4/1990 | |
| JP | H02131422 | A | 5/1990 | |
| JP | H02131422 | U | 11/1990 | |
| JP | H0460220 | A | 2/1992 | |
| JP | H05123349 | A | 5/1993 | |
| JP | H05123350 | A | 5/1993 | |
| JP | H0626264 | U | 4/1994 | |
| JP | 3087938 | B2 | 10/1995 | |
| JP | H085630 | A | 1/1996 | |
| JP | H1040141 | A | 2/1998 | |

(56) References Cited

FOREIGN PATENT DOCUMENTS

| | | | |
|---|---|---|---|
| JP | H10225430 | A | 8/1998 |
| JP | H11113946 | A | 4/1999 |
| JP | H11290365 | A | 10/1999 |
| JP | 2000116690 | A | 4/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003528691 | A | 9/2003 |
| JP | 2004057578 | A | 2/2004 |
| JP | 2004130056 | A | 4/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011218130 | A | 11/2011 |
| JP | 2011224070 | A | 11/2011 |
| JP | 3175719 | U | 4/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 2017512603 | A | 5/2017 |
| JP | 2017201272 | A | 11/2017 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020520775 | A | 7/2020 |
| JP | 2021007472 | A | 1/2021 |
| JP | 2021120686 | A | 8/2021 |
| JP | 2021522009 | A | 8/2021 |
| JP | 2021522013 | A | 8/2021 |
| JP | 7129493 | B2 | 8/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090104426 | A | 10/2009 |
| KR | 20090110359 | A | 10/2009 |
| KR | 20120005922 | A | 1/2012 |
| KR | 20140039485 | A | 4/2014 |
| KR | 101432639 | B1 | 8/2014 |
| KR | 20180106659 | A | 10/2018 |
| KR | 20180108774 | A | 10/2018 |
| PT | 2068717 | E | 6/2013 |
| SE | 505542 | C2 | 9/1997 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |

(56) References Cited

FOREIGN PATENT DOCUMENTS

| | | | |
|---|---|---|---|
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022031943 | A1 | 2/2022 |
| WO | 2022035745 | A1 | 2/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150360 | A1 | 7/2022 |

(56)     References Cited

FOREIGN PATENT DOCUMENTS

| WO | 2022150463 A1 | 7/2022 |
|---|---|---|
| WO | 2022159392 A1 | 7/2022 |
| WO | 2022170182 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022204000 A1 | 9/2022 |
| WO | 2022216507 A1 | 10/2022 |
| WO | 2022216776 A1 | 10/2022 |
| WO | 2022222030 A1 | 10/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023023777 A1 | 3/2023 |
| WO | 2023034139 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023191764 A1 | 10/2023 |
| WO | 2023244238 A1 | 12/2023 |
| WO | 2024058788 A1 | 3/2024 |

OTHER PUBLICATIONS

Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/453,260 mailed Dec. 22, 2023.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/662,700 mailed Jan. 30, 2023.
Corrected Notice of Allowability for U.S. Appl. No. 16/369,676 mailed Dec. 7, 2023.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/449,039 mailed Nov. 21, 2023.
Final Office Action for U.S. Appl. No. 16/452,145 mailed Mar. 25, 2022.
Final Office Action for U.S. Appl. No. 16/452,258 mailed Dec. 21, 2023.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/904,868 mailed Mar. 10, 2022.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.

(56) References Cited

OTHER PUBLICATIONS

Final Office Action for U.S. Appl. No. 18/139,523 mailed Dec. 22, 2023.

Final Office Action for U.S. Appl. No. 18/140,751 mailed Jan. 17, 2024.

Final Office Action for U.S. Appl. No. 18/164,800 mailed Dec. 6, 2023.

International Search Report and Written Opinion from International Application No. PCT/IB2021/057173 mailed Nov. 5, 2021.

International Search Report and Written Opinion from International Application No. PCT/US2020/057562 mailed Jan. 27, 2021.

International Search Report and Written Opinion from International Application No. PCT/US2021/026607 mailed Jul. 29, 2021.

International Search Report and Written Opinion from International Application No. PCT/US2021/039866 mailed Oct. 7, 2021.

International Search Report and Written Opinion from International Application No. PCT/US2021/045188 mailed Jan. 26, 2022.

International Search Report and Written Opinion from International Application No. PCT/US2021/048661 mailed Feb. 14, 2022.

International Search Report and Written Opinion from International Application No. PCT/US2021/049404 mailed Jan. 18, 2022.

International Search Report and Written Opinion from International Application No. PCT/US2021/051456 mailed Jan. 19, 2022.

International Search Report and Written Opinion from International Application No. PCT/US2021/053593 mailed Apr. 11, 2022.

International Search Report and Written Opinion from International Application No. PCT/US2021/055515 mailed Jan. 28, 2022.

International Search Report and Written Opinion from International Application No. PCT/US2021/056566 mailed Feb. 11, 2022.

International Search Report and Written Opinion from International Application No. PCT/US2021/060993 mailed Mar. 18, 2022.

International Search Report and Written Opinion from International Application No. PCT/US2021/062440 mailed Mar. 28, 2022.

International Search Report and Written Opinion from International Application No. PCT/US2022/011108 mailed Apr. 22, 2022.

International Search Report and Written Opinion from International Application No. PCT/US2022/011281 mailed Apr. 25, 2022.

International Search Report and Written Opinion from International Application No. PCT/US2022/011419 mailed Jun. 7, 2022.

International Search Report and Written Opinion from International Application No. PCT/US2022/011421 mailed Jun. 13, 2022.

International Search Report and Written Opinion from International Application No. PCT/US2022/012794 mailed May 3, 2022.

International Search Report and Written Opinion from International Application No. PCT/US2022/014285 mailed Sep. 28, 2022.

International Search Report and Written Opinion from International Application No. PCT/US2022/014749 mailed Sep. 28, 2022.

International Search Report and Written Opinion from International Application No. PCT/US2022/015026 mailed Oct. 31, 2022.

International Search Report and Written Opinion from International Application No. PCT/US2022/015045 mailed Sep. 9, 2022.

International Search Report and Written Opinion from International Application No. PCT/US2022/015073 mailed Sep. 8, 2022.

International Search Report and Written Opinion from International Application No. PCT/US2022/015418 mailed Nov. 11, 2022.

International Search Report and Written Opinion from International Application No. PCT/US2022/015420 mailed Nov. 18, 2022.

International Search Report and Written Opinion from International Application No. PCT/US2022/015471 mailed May 16, 2022.

International Search Report and Written Opinion from International Application No. PCT/US2022/015492 mailed Apr. 26, 2022.

International Search Report and Written Opinion from International Application No. PCT/US2022/015781 mailed May 6, 2022.

International Search Report and Written Opinion from International Application No. PCT/US2022/016942 mailed Jun. 8, 2022.

International Search Report and Written Opinion from International Application No. PCT/US2022/018159 mailed Dec. 12, 2022.

International Search Report and Written Opinion from International Application No. PCT/US2022/018170 mailed May 31, 2022.

International Search Report and Written Opinion from International Application No. PCT/US2022/019254 mailed Jun. 7, 2022.

International Search Report and Written Opinion from International Application No. PCT/US2022/019480 mailed Jun. 13, 2022.

International Search Report and Written Opinion from International Application No. PCT/US2022/021103 mailed Jun. 23, 2022.

International Search Report and Written Opinion from International Application No. PCT/US2022/022111 mailed Oct. 26, 2022.

International Search Report and Written Opinion from International Application No. PCT/US2022/023594 mailed Jul. 12, 2022.

International Search Report and Written Opinion from International Application No. PCT/US2022/026667 mailed Aug. 22, 2022.

International Search Report and Written Opinion from International Application No. PCT/US2022/030685 mailed Oct. 31, 2022.

International Search Report and Written Opinion from International Application No. PCT/US2022/031032 mailed Sep. 9, 2022.

International Search Report and Written Opinion from International Application No. PCT/US2022/032424 mailed Oct. 11, 2022.

International Search Report and Written Opinion from International Application No. PCT/US2022/034457 mailed Oct. 12, 2022.

International Search Report and Written Opinion from International Application No. PCT/US2022/034744 mailed Dec. 9, 2022.

International Search Report and Written Opinion from International Application No. PCT/US2022/039018 mailed Jan. 10, 2023.

International Search Report and Written Opinion from International Application No. PCT/US2022/039022 mailed Jan. 10, 2023.

International Search Report and Written Opinion from International Application No. PCT/US2022/039711 mailed Jan. 12, 2023.

International Search Report and Written Opinion from International Application No. PCT/US2022/039714 mailed Nov. 22, 2022.

International Search Report and Written Opinion from International Application No. PCT/US2022/041085 mailed Mar. 16, 2023.

International Search Report and Written Opinion from International Application No. PCT/US2022/041688 mailed Nov. 21, 2022.

International Search Report and Written Opinion from International Application No. PCT/US2022/042719 mailed Dec. 5, 2022.

International Search Report and Written Opinion from International Application No. PCT/US2022/042725 mailed Dec. 19, 2022.

International Search Report and Written Opinion from International Application No. PCT/US2022/043818 mailed Mar. 24, 2023.

International Search Report and Written Opinion from International Application No. PCT/US2022/044107 mailed Dec. 23, 2022.

International Search Report and Written Opinion from International Application No. PCT/US2022/044208 mailed May 8, 2023.

International Search Report and Written Opinion from International Application No. PCT/US2022/044212 mailed Jan. 20, 2023.

International Search Report and Written Opinion from International Application No. PCT/US2022/044243 mailed Feb. 24, 2023.

International Search Report and Written Opinion from International Application No. PCT/US2022/049300 mailed Jun. 6, 2023.

International Search Report and Written Opinion from International Application No. PCT/US2022/050909 mailed Jul. 24, 2023.

International Search Report and Written Opinion from International Application No. PCT/US2023/012696 mailed Jul. 6, 2023.

International Search Report and Written Opinion from International Application No. PCT/US2023/018474 mailed Sep. 11, 2023.

International Search Report and Written Opinion from International Application No. PCT/US2023/024805 mailed Dec. 14, 2023.

Issue Notification for U.S. Appl. No. 16/245,726 mailed Oct. 18, 2023.

Issue Notification for U.S. Appl. No. 16/899,956 mailed Mar. 29, 2023.

Issue Notification for U.S. Appl. No. 16/905,400 mailed Nov. 30, 2022.

Issue Notification for U.S. Appl. No. 17/088,272 mailed Jun. 15, 2022.

Issue Notification for U.S. Appl. No. 17/330,657 mailed Jun. 22, 2022.

Issue Notification for U.S. Appl. No. 17/461,036 mailed Oct. 11, 2023.

Issue Notification for U.S. Appl. No. 17/663,046 mailed Dec. 20, 2023.

(56) References Cited

OTHER PUBLICATIONS

Non-Final Office Action for U.S. Appl. No. 16/369,676 mailed Mar. 31, 2022.

Non-Final Office Action for U.S. Appl. No. 16/433,773 mailed Apr. 11, 2023.

Non-Final Office Action for U.S. Appl. No. 16/433,773 mailed Apr. 21, 2022.

Non-Final Office Action for U.S. Appl. No. 16/449,039 mailed Apr. 27, 2023.

Non-Final Office Action for U.S. Appl. No. 16/452,145 mailed Mar. 28, 2023.

Non-Final Office Action for U.S. Appl. No. 16/452,145 mailed Nov. 2, 2023.

Non-Final Office Action for U.S. Appl. No. 16/452,258 mailed Apr. 26, 2023.

Non-Final Office Action for U.S. Appl. No. 16/478,180 mailed Dec. 20, 2022.

Non-Final Office Action for U.S. Appl. No. 16/478,180 mailed Nov. 7, 2023.

Non-Final Office Action for U.S. Appl. No. 16/904,868 mailed Mar. 15, 2023.

Non-Final Office Action for U.S. Appl. No. 16/905,400 mailed Apr. 27, 2022.

Non-Final Office Action for U.S. Appl. No. 17/051,399 mailed Aug. 18, 2023.

Non-Final Office Action for U.S. Appl. No. 17/051,550 mailed Dec. 15, 2022.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,585 mailed Mar. 29, 2023.

Non-Final Office Action for U.S. Appl. No. 17/051,600 mailed Jan. 17, 2024.

Non-Final Office Action for U.S. Appl. No. 17/179,116 mailed Mar. 24, 2023.

Non-Final Office Action for U.S. Appl. No. 17/326,980 mailed Jul. 11, 2023.

Non-Final Office Action for U.S. Appl. No. 17/444,792 mailed Feb. 10, 2023.

Non-Final Office Action for U.S. Appl. No. 17/444,792 mailed Nov. 17, 2023.

Non-Final Office Action for U.S. Appl. No. 17/446,256 mailed Apr. 13, 2023.

Non-Final Office Action for U.S. Appl. No. 17/446,654 mailed Sep. 8, 2023.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/448,811 mailed Mar. 1, 2023.

Non-Final Office Action for U.S. Appl. No. 17/450,864 mailed May 10, 2023.

Non-Final Office Action for U.S. Appl. No. 17/451,345 mailed Dec. 7, 2022.

Non-Final Office Action for U.S. Appl. No. 17/451,345 mailed Jan. 17, 2024.

Non-Final Office Action for U.S. Appl. No. 17/451,354 mailed May 3, 2023.

Non-Final Office Action for U.S. Appl. No. 17/453,260 mailed Mar. 14, 2023.

Non-Final Office Action for U.S. Appl. No. 17/453,560 mailed Oct. 16, 2023.

Non-Final Office Action for U.S. Appl. No. 17/501,591 mailed Apr. 25, 2023.

Non-Final Office Action for U.S. Appl. No. 17/645,821 mailed Oct. 25, 2023.

Non-Final Office Action for U.S. Appl. No. 17/646,771 mailed Jul. 5, 2023.

Non-Final Office Action for U.S. Appl. No. 17/653,137 mailed Apr. 7, 2023.

Non-Final Office Action for U.S. Appl. No. 17/653,137 mailed Jan. 18, 2024.

Non-Final Office Action for U.S. Appl. No. 17/655,464 mailed Mar. 14, 2023.

Non-Final Office Action for U.S. Appl. No. 17/657,474 mailed Sep. 12, 2023.

Non-Final Office Action for U.S. Appl. No. 17/661,090 mailed Jul. 6, 2023.

Non-Final Office Action for U.S. Appl. No. 17/662,700 mailed Jul. 22, 2022.

Non-Final Office Action for U.S. Appl. No. 17/663,330 mailed Jun. 29, 2023.

Non-Final Office Action for U.S. Appl. No. 17/664,487 mailed Jun. 8, 2023.

Non-Final Office Action for U.S. Appl. No. 17/808,354 mailed Nov. 28, 2023.

Non-Final Office Action for U.S. Appl. No. 18/134,857 mailed Jan. 25, 2024.

Non-Final Office Action for U.S. Appl. No. 18/139,523 mailed Aug. 17, 2023.

Non-Final Office Action for U.S. Appl. No. 18/140,163 mailed Nov. 9, 2023.

Non-Final Office Action for U.S. Appl. No. 18/140,751 mailed Sep. 14, 2023.

Non-Final Office Action for U.S. Appl. No. 18/198,464 mailed Dec. 7, 2023.

Notice of Allowance for U.S. Appl. No. 16/245,726 mailed Jul. 6, 2023.

Notice of Allowance for U.S. Appl. No. 16/369,676 mailed Nov. 14, 2023.

Notice of Allowance for U.S. Appl. No. 16/449,039 mailed Dec. 15, 2022.

Notice of Allowance for U.S. Appl. No. 16/899,956 mailed Apr. 19, 2022.

Notice of Allowance for U.S. Appl. No. 16/899,956 mailed Aug. 10, 2022.

Notice of Allowance for U.S. Appl. No. 16/899,956 mailed Dec. 1, 2022.

Notice of Allowance for U.S. Appl. No. 16/905,400 mailed Aug. 17, 2022.

Notice of Allowance for U.S. Appl. No. 17/051,554 mailed Jul. 6, 2023.

Notice of Allowance for U.S. Appl. No. 17/051,554 mailed Oct. 18, 2023.

Notice of Allowance for U.S. Appl. No. 17/088,272 mailed Mar. 4, 2022.

Notice of Allowance for U.S. Appl. No. 17/330,657 mailed Mar. 16, 2022.

Notice of Allowance for U.S. Appl. No. 17/461,036 mailed Feb. 22, 2023.

Notice of Allowance for U.S. Appl. No. 17/461,036 mailed Jun. 30, 2023.

Notice of Allowance for U.S. Appl. No. 17/461,036 mailed Oct. 6, 2022.

Notice of Allowance for U.S. Appl. No. 17/662,700 mailed Jul. 28, 2023.

Notice of Allowance for U.S. Appl. No. 17/662,700 mailed Mar. 28, 2023.

Notice of Allowance for U.S. Appl. No. 17/662,700 mailed Nov. 15, 2023.

Notice of Allowance for U.S. Appl. No. 17/663,046 mailed Jan. 30, 2023.

Notice of Allowance for U.S. Appl. No. 18/299,788 mailed Jul. 24, 2023.

Notice of Allowance for U.S. Appl. No. 18/299,788 mailed Nov. 6, 2023.

Notice of Allowance for U.S. Appl. No. 29/741,751 mailed Jun. 9, 2022.

(56) References Cited

OTHER PUBLICATIONS

Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 18/134,857 mailed Oct. 23, 2023.
Text Messages to Lorena Eckert Re Prototype PureWick Holder dated Apr. 16, 2022.
U.S. Appl. No. 15/384,196, filed Dec. 19, 2016.
U.S. Appl. No. 17/451,719, filed Oct. 19, 2021.
U.S. Appl. No. 17/631,619, filed Jan. 31, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 62/923,279, filed Oct. 18, 2019.
U.S. Appl. No. 62/926,767, filed Oct. 28, 2019.
U.S. Appl. No. 62/967,158, filed Jan. 26, 2020.
U.S. Appl. No. 62/991,754, filed Mar. 19, 2020.
U.S. Appl. No. 63/008,112, filed Apr. 10, 2020.
U.S. Appl. No. 63/094,646, filed Oct. 21, 2020.
U.S. Appl. No. 63/150,640, filed Feb. 18, 2021.
U.S. Appl. No. 63/191,558, filed May 21, 2021.
U.S. Appl. No. 63/192,289, filed May 24, 2021.
U.S. Appl. No. 63/208,262, filed Jun. 8, 2021.
U.S. Appl. No. 63/230,897, filed Aug. 9, 2021.
U.S. Appl. No. 63/241,328, filed Sep. 7, 2021.
U.S. Appl. No. 63/308,190, filed Feb. 9, 2022.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical , Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/444,792 mailed Jul. 8, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,345 mailed Jul. 3, 2024.

(56)             References Cited

OTHER PUBLICATIONS

Advisory Action for U.S. Appl. No. 17/451,354 mailed Jan. 30, 2024.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 17/326,980 mailed Feb. 8, 2024.
Corrected Notice of Allowability for U.S. Appl. No. 17/501,591 mailed Aug. 9, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Final Office Action for U.S. Appl. No. 16/433,773 mailed Sep. 9, 2024.
Final Office Action for U.S. Appl. No. 16/478,180 mailed Feb. 28, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/808,354 mailed Apr. 10, 2024.
Final Office Action for U.S. Appl. No. 18/134,857 mailed Jul. 25, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.

International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/904,868 mailed Mar. 12, 2024.
Non-Final Office Action for U.S. Appl. No. 17/179,116 mailed Feb. 26, 2024.
Non-Final Office Action for U.S. Appl. No. 17/378,015 mailed Jul. 5, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/614,173 mailed Sep. 24, 2024.

(56) References Cited

OTHER PUBLICATIONS

Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,314 mailed Aug. 29, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/749,340 mailed Aug. 14, 2024.
Non-Final Office Action for U.S. Appl. No. 17/758,316 mailed Aug. 28, 2024.
Non-Final Office Action for U.S. Appl. No. 18/003,029 mailed Mar. 26, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 17/051,550 mailed Feb. 7, 2024.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/657,474 mailed Mar. 5, 2024.

Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/389,009 mailed Aug. 28, 2024.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/667,097 mailed Mar. 20, 2024.
Restriction Requirement for U.S. Appl. No. 17/878,268 mailed Sep. 20, 2024.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/013,822, filed Sep. 7, 2020.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/426,795, filed Jan. 30, 2024.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 63/561,893, filed Dec. 11, 2023.
U.S. Appl. No. 63/568,615, filed Mar. 22, 2024.
U.S. Appl. No. 63/683,428, filed Aug. 15, 2024.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (Polyox) in Hydrophilic Matrices", Hydrophilic Matrix Tablets for Oral Controlled Release, AAPS Advances in the Pharmaceutical Sciences vol. 16, 2014, pp. 123-141.

(56) References Cited

OTHER PUBLICATIONS

Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.

(56)       References Cited

OTHER PUBLICATIONS

International Search Report and Written Opinion from International Application No. PCT/US2021/047536 mailed Dec. 23, 2021.

International Search Report and Written Opinion from International Application No. PCT/US2021/048211 mailed Dec. 22, 2021.

Issue Notification for U.S. Appl. No. 14/952,591 mailed Jul. 28, 2021.

Issue Notification for U.S. Appl. No. 15/171,968 mailed Mar. 3, 2021.

Issue Notification for U.S. Appl. No. 15/221,106 mailed Jul. 24, 2019.

Issue Notification for U.S. Appl. No. 15/238,427 mailed Jul. 24, 2019.

Issue Notification for U.S. Appl. No. 15/260,103 mailed Aug. 7, 2019.

Issue Notification for U.S. Appl. No. 15/611,587 mailed Feb. 20, 2019.

Issue Notification for U.S. Appl. No. 15/612,325 mailed Mar. 24, 2021.

Issue Notification for U.S. Appl. No. 29/624,661 mailed Aug. 4, 2021.

Non-Final Office Action for U.S. Appl. No. 14/592,591 mailed Mar. 20, 2020.

Non-Final Office Action for U.S. Appl. No. 14/722,613 mailed Jun. 13, 2019.

Non-Final Office Action for U.S. Appl. No. 14/947,759 mailed Mar. 17, 2016.

Non-Final Office Action for U.S. Appl. No. 14/952,591 mailed Aug. 1, 2017.

Non-Final Office Action for U.S. Appl. No. 14/952,591 mailed Mar. 20, 2020.

Non-Final Office Action for U.S. Appl. No. 14/952,591 mailed Mar. 21, 2019.

Non-Final Office Action for U.S. Appl. No. 14/952,591 mailed Sep. 28, 2018.

Non-Final Office Action for U.S. Appl. No. 15/171,968 mailed May 11, 2020.

Non-Final Office Action for U.S. Appl. No. 15/171,968 mailed Aug. 20, 2019.

Non-Final Office Action for U.S. Appl. No. 15/171,968 mailed Jun. 12, 2018.

Non-Final Office Action for U.S. Appl. No. 15/221,106 mailed Jun. 5, 2018.

Non-Final Office Action for U.S. Appl. No. 15/238,427 mailed Aug. 8, 2018.

Non-Final Office Action for U.S. Appl. No. 15/260,103 mailed Sep. 26, 2018.

Non-Final Office Action for U.S. Appl. No. 15/611,587 mailed Dec. 29, 2017.

Non-Final Office Action for U.S. Appl. No. 15/611,587 mailed Jul. 13, 2018.

Non-Final Office Action for U.S. Appl. No. 15/612,325 mailed Mar. 19, 2020.

Non-Final Office Action for U.S. Appl. No. 16/449,039 mailed Dec. 8, 2021.

Non-Final Office Action for U.S. Appl. No. 16/452,145 mailed Sep. 28, 2021.

Non-Final Office Action for U.S. Appl. No. 16/452,258 mailed Sep. 28, 2021.

Non-Final Office Action for U.S. Appl. No. 16/478,180 mailed Oct. 22, 2021.

Non-Final Office Action for U.S. Appl. No. 16/899,956 mailed Oct. 16, 2020.

Non-Final Office Action for U.S. Appl. No. 16/899,956 mailed Sep. 2, 2021.

Non-Final Office Action for U.S. Appl. No. 16/904,868 mailed Nov. 25, 2020.

Non-Final Office Action for U.S. Appl. No. 16/904,868 mailed Oct. 5, 2021.

Non-Final Office Action for U.S. Appl. No. 16/905,400 mailed Dec. 2, 2020.

Non-Final Office Action for U.S. Appl. No. 16/905,400 mailed Jul. 22, 2021.

Non-Final Office Action for U.S. Appl. No. 17/088,272 mailed Jan. 25, 2021.

Non-Final Office Action for U.S. Appl. No. 17/330,657 mailed Aug. 11, 2021.

Non-Final Office Action for U.S. Appl. No. 29/624,661 mailed Jul. 18, 2019.

Non-Final Office Action for U.S. Appl. No. 29/694,002 mailed Jun. 24, 2020.

Non-Final Office Action for U.S. Appl. No. 29/741,751 mailed Jan. 18, 2022.

Notice of Allowance for U.S. Appl. No. 14/952,591 mailed Apr. 5, 2021.

Notice of Allowance for U.S. Appl. No. 14/952,591 mailed Jul. 8, 2021.

Notice of Allowance for U.S. Appl. No. 15/171,968 mailed Feb. 16, 2021.

Notice of Allowance for U.S. Appl. No. 15/171,968 mailed Nov. 6, 2020.

Notice of Allowance for U.S. Appl. No. 15/221,106 mailed May 1, 2019.

Notice of Allowance for U.S. Appl. No. 15/238,427 mailed May 23, 2019.

Notice of Allowance for U.S. Appl. No. 15/260,103 mailed Jun. 7, 2019.

Notice of Allowance for U.S. Appl. No. 15/611,587 mailed Dec. 21, 2018.

Notice of Allowance for U.S. Appl. No. 15/612,325 mailed Feb. 19, 2021.

Notice of Allowance for U.S. Appl. No. 15/612,325 mailed Jan. 21, 2021.

Notice of Allowance for U.S. Appl. No. 16/899,956 mailed Dec. 29, 2021.

Notice of Allowance for U.S. Appl. No. 17/088,272 mailed Aug. 5, 2021.

Notice of Allowance for U.S. Appl. No. 17/088,272 mailed Nov. 24, 2021.

Notice of Allowance for U.S. Appl. No. 17/330,657 mailed Nov. 26, 2021.

Notice of Allowance for U.S. Appl. No. 29/624,661 mailed Apr. 28, 2021.

Notice of Allowance for U.S. Appl. No. 29/624,661 mailed Jul. 10, 2020.

Notice of Allowance for U.S. Appl. No. 29/624,661 mailed May 14, 2020.

Notice of Allowance for U.S. Appl. No. 29/624,661 mailed Sep. 29, 2020.

Notice of Allowance for U.S. Appl. No. 29/694,002 mailed Apr. 29, 2021.

Notice of Allowance for U.S. Appl. No. 29/694,002 mailed Jan. 29, 2021.

Notice of Allowance for U.S. Appl. No. 29/694,002 mailed Oct. 16, 2020.

Notice to File Missing Parts for U.S. Appl. No. 17/179,116 mailed Mar. 3, 2021.

Restriction Requirement for U.S. Appl. No. 16/478,180 mailed May 25, 2021.

U.S. Appl. No. 14/433,773, filed Apr. 3, 2020.

U.S. Appl. No. 14/625,469, filed Feb. 28, 2015.

U.S. Appl. No. 14/947,759, filed Nov. 20, 2015.

U.S. Appl. No. 14/952,591, filed Nov. 25, 2015.

U.S. Appl. No. 15/171,968, filed Jun. 2, 2016.

U.S. Appl. No. 15/221,106, filed Jul. 27, 2016.

U.S. Appl. No. 15/260,103, filed Sep. 8, 2016.

U.S. Appl. No. 15/611,587, filed Jun. 1, 2017.

U.S. Appl. No. 15/612,325, filed Jun. 2, 2017.

U.S. Appl. No. 16/245,726, filed Jan. 11, 2019.

U.S. Appl. No. 16/369,676, filed Mar. 29, 2019.

U.S. Appl. No. 16/433,773, filed Jun. 6, 2019.

U.S. Appl. No. 16/449,039, filed Jun. 21, 2019.

(56) References Cited

OTHER PUBLICATIONS

U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/645,821, filed Dec. 23, 2021.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.

U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.

(56) References Cited

OTHER PUBLICATIONS

Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. No's 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Corrected Notice of Allowability for U.S. Appl. No. 17/330,657 mailed Dec. 9, 2021.
Non-Final Office Action for U.S. Appl. No. 16/245,726 mailed Jan. 21, 2022.
Restriction Requirement for U.S. Appl. No. 16/433,773 mailed Dec. 7, 2021.
U.S. Appl. No. 17/394,055, filed Aug. 4, 2021.
U.S. Appl. No. 17/646,771, filed Jan. 3, 2022.
U.S. Appl. No. 62/967,977, filed Jan. 30, 2020.
U.S. Appl. No. 63/138,878, filed Jan. 19, 2021.
U.S. Appl. No. 63/299,208, filed Jan. 13, 2022.
Exhibit B to PureWick's Supplemental Response to Interrogatory No. 6: U.S. Pat. No. 8,287,508, 25 pages.
Exhibit B to PureWick's Supplemental Response to Interrogatory No. 6: U.S. Pat. No. 10,390,989, 26 pages.
Sage's Supplemental Statement Regarding References and Combinations, 3 pages.
Exhibit B to PureWick's Supplemental Response to Interrogatory No. 6: U.S. Pat. No. 10,226,376, 38 pages.
Sixth Supplemental Responses to Sage Products' First Set of Interrogatories (No. 1-11) to PureWick Corporation, Apr. 2021, 39 pages.
Seventh Supplemental Responses to Sage Products' First Set of Interrogatories (No. 1-11) to PureWick Corporation, Apr. 2021, 41 pages.
Sage's Second Notice of Deposition of PureWick Corporation, Feb. 2021, 10 pages.
Sage's First Notice of Deposition of PureWick Corporation, Feb. 2021, 14 pages.
Exhibit A to PureWick's Fourth Supplemental Response to Interrogatory No. 3, Mar. 2021, 21 pages.
PureWick's Supplemental Response to Interrogatory No. 6 Exhibit C: U.S. Pat. No. 6,287,508, Sep. 2020, 21 pages.
Autumn , et al., "Frictional adhesion: a new angle on gecko attachment", The Journal of Experimental Biology, 2006, pp. 3569-3579.

(56)        References Cited

OTHER PUBLICATIONS

Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jennewein , "Connect Graduates 7 Startups in Tech, Life Sciences", https://timesofsandiego.com/business/2015/08/16/connect-graduates-7-startups-in-tech-life-sciences/, Aug. 2015, 2 pages.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Parness , et al., "A microfabricated wedge-shaped adhesive array displaying gecko-like dynamic adhesion, directionality", J.R. Soc. Interface, 2009, pp. 1223-1232.
Tsipenyuk , et al., "Use of biomimetic hexagonal surface texture in friction against lubricated skin", Journal of The Royal Society—Interface, 2014, pp. 1-6.
Advisory Action for U.S. Appl. No. 17/051,585 mailed Oct. 8, 2024.
Advisory Action for U.S. Appl. No. 17/446,256 mailed Nov. 19, 2024.
Advisory Action for U.S. Appl. No. 17/597,673 mailed Jan. 7, 2025.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/646,771 mailed Jan. 17, 2025.
Corrected Notice of Allowability for U.S. Appl. No. 18/426,795 mailed Dec. 4, 2024.
Final Office Action for U.S. Appl. No. 16/452,258 mailed Jan. 6, 2025.
Final Office Action for U.S. Appl. No. 17/446,654 mailed Dec. 18, 2024.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/653,314 mailed Jan. 30, 2025.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 18/003,029 mailed Oct. 22, 2024.
Final Office Action for U.S. Appl. No. 18/164,800 mailed Oct. 22, 2024.
Issue Notification for U.S. Appl. No. 16/369,676 mailed Oct. 2, 2024.
Issue Notification for U.S. Appl. No. 16/452,145 mailed Oct. 23, 2024.
Issue Notification for U.S. Appl. No. 17/179,116 mailed Dec. 25, 2024.
Issue Notification for U.S. Appl. No. 17/447,123 mailed Nov. 13, 2024.
Issue Notification for U.S. Appl. No. 17/450,864 mailed Jan. 8, 2025.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/198,464 mailed Nov. 20, 2024.
Issue Notification for U.S. Appl. No. 18/389,009 mailed Dec. 18, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/653,137 mailed Jan. 28, 2025.
Non-Final Office Action for U.S. Appl. No. 17/653,920 mailed Nov. 27, 2024.
Non-Final Office Action for U.S. Appl. No. 17/757,311 mailed Oct. 22, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/663,330 mailed Nov. 20, 2024.
Notice of Allowance for U.S. Appl. No. 17/596,629 mailed Jan. 29, 2025.
Notice of Allowance for U.S. Appl. No. 18/140,751 mailed Nov. 1, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/754,736 mailed Nov. 20, 2024.

(56) References Cited

OTHER PUBLICATIONS

Restriction Requirement for U.S. Appl. No. 17/756,201 mailed Oct. 4, 2024.

Restriction Requirement for U.S. Appl. No. 17/758,152 mailed Nov. 5, 2024.

Restriction Requirement for U.S. Appl. No. 17/809,083 mailed Dec. 31, 2024.

U.S. Appl. No. 18/903,592, filed Oct. 1, 2024.

U.S. Appl. No. 18/925,921, filed Oct. 24, 2024.

U.S. Appl. No. 18/930,014, filed Oct. 29, 2024.

U.S. Appl. No. 18/931,853, filed Oct. 30, 2024.

U.S. Appl. No. 18/951,944, filed Nov. 19, 2024.

U.S. Appl. No. 18/957,011, filed Nov. 22, 2024.

U.S. Appl. No. 18/974,367, filed Dec. 9, 2024.

U.S. Appl. No. 18/982,930, filed Dec. 16, 2024.

U.S. Appl. No. 19/038,774, filed Jan. 28, 2025.

U.S. Appl. No. 19/039,165, filed Jan. 28, 2025.

U.S. Appl. No. 63/564,696, filed Mar. 13, 2024.

U.S. Appl. No. 63/181,709, filed Apr. 29, 2021.

U.S. Appl. No. 63/711,438, filed Oct. 24, 2024.

U.S. Appl. No. 63/711,445, filed Oct. 24, 2024.

U.S. Appl. No. 63/720,004, filed Nov. 13, 2024.

"Dictionary.com, ABUT Definition and Meaning", Dictionary.com, https://www.dictionary.com/browse/abut, 2024, 1 page.

* cited by examiner

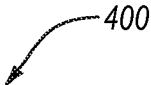

Positioning an opening of a fluid collection device adjacent to a female urethra or around a male urethra, the fluid collection device including: a fluid impermeable barrier having an outer surface and an inner surface, the inner surface at least partially defining a chamber, the fluid impermeable barrier also defining an opening configured to be positioned adjacent to a female urethra or have a male urethra positioned therethrough; a wicking material disposed within the fluid impermeable barrier; a conduit including an inlet and an outlet, the outlet being fluidly coupled to a fluid storage container and the inlet being positioned in a portion of the chamber selected to be at a gravimetrically low point of the fluid collection device when worn by a user; and an antimicrobial material carried by one or more of the fluid impermeable barrier or the wicking material     ~410

Receiving fluid from the female urethra or the male urethra into the chamber of the fluid collection device     ~420

Applying suction with a vacuum source effective to suction the fluid from the chamber via a conduit disposed therein and fluidly coupled to the vacuum source     ~430

FIG. 4

FLUID COLLECTION DEVICES, SYSTEMS, AND METHODS

CROSS REFERENCE TO RELATED APPLICATIONS

This Application is a U.S. Nationalization of PCT International Application No. PCT/US2020/041249 filed on 8 Jul. 2020, which claims priority to U.S. Patent Application No. 62/873,048 filed on 11 Jul. 2019, the disclosure of each of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection devices continue to seek new and improved devices, systems, and methods to collect urine.

SUMMARY

Embodiments disclosed herein are related to devices, systems, and methods of using fluid collection devices. In an embodiment, a fluid collection device is disclosed. The fluid collection device includes a fluid impermeable barrier having an outer surface and an inner surface, the inner surface at least partially defining a chamber, the fluid impermeable barrier also defining an opening extending therethrough, the opening configured to be positioned adjacent to a female urethra or have a male urethra positioned therethrough. The fluid collection device includes a wicking material disposed in the chamber. The fluid collection device includes an antimicrobial material carried by one or more of the fluid impermeable barrier or the wicking material.

In an embodiment, a fluid collection system is disclosed. The fluid collection system includes a fluid storage container configured to hold a fluid. The fluid collection system includes a fluid collection device fluidly coupled to the fluid storage container. The fluid collection device includes a fluid impermeable barrier having an outer surface and an inner surface, the inner surface at least partially defining a chamber, the fluid impermeable barrier also defining an opening configured to be positioned adjacent to a female urethra or have a male urethra positioned therethrough. The fluid collection device includes a wicking material disposed within the fluid impermeable barrier. The fluid collection device includes a conduit including an inlet and an outlet, the outlet being fluidly coupled to the fluid storage container and the inlet being positioned in a portion of the chamber selected to be at a gravimetrically low point of the fluid collection device when worn by a user. The fluid collection device includes an antimicrobial material carried by one or more of the fluid impermeable barrier or the wicking material. The fluid collection system includes a vacuum source fluidly coupled to one or more of the fluid storage container or the fluid collection device via the conduit, the vacuum source configured to draw fluid from the fluid collection device via the conduit.

In an embodiment, a method to collect fluid is disclosed. The method includes positioning an opening of a fluid collection device adjacent to a female urethra or around a male urethra. The fluid collection device of the method includes a fluid impermeable barrier having an outer surface and an inner surface, the inner surface at least partially defining a chamber, the fluid impermeable barrier also defining an opening configured to be positioned adjacent to a female urethra or have a male urethra positioned therethrough. The fluid collection device of the method includes a wicking material disposed within the fluid impermeable barrier. The fluid collection device of the method includes a conduit including an inlet and an outlet, the outlet being fluidly coupled to a fluid storage container and the inlet being positioned in a portion of the chamber selected to be at a gravimetrically low point of the fluid collection device when worn by a user. The fluid collection device of the method includes an antimicrobial material carried by one or more of the fluid impermeable barrier or the wicking material. The method includes receiving fluid from the female urethra or the male urethra into the chamber of the fluid collection device. The method includes applying suction with a vacuum source effective to suction the fluid from the chamber via a conduit disposed therein and fluidly coupled to the vacuum source.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 4 is a flow diagram of a method to collect fluid, according to an embodiment.

DETAILED DESCRIPTION

Embodiments disclosed herein are related to devices, systems, and methods of using fluid collection devices and systems. The devices, systems, and methods of using fluid collection devices and systems include an antimicrobial material therein or thereon to prevent infections, lower microbial growth rates, and control odors in the fluid collection device.

In some examples, a fluid collection device includes a fluid impermeable barrier that at least partially defines a chamber. The fluid impermeable barrier also defines an opening extending therethrough that is configured to be positioned adjacent to a female urethra or have a male urethra positioned therethrough. The fluid collection device includes a wicking material disposed within the chamber. The fluid collection device may also include a conduit disposed in the chamber. The fluid collection device includes an anti-microbial material carried by one or more of the fluid impermeable barrier, the wicking material, or the conduit. The anti-microbial material may be disposed in, on, or incorporated into any of the components of the fluid collection device.

The fluid collection devices disclosed herein are configured to collect fluid(s) from an individual. The fluid collected by the fluid collection devices may include urine. The fluid(s) collected by the fluid collection devices may include at least one of vaginal discharge, penile discharge, reproductive fluids, blood, sweat, or other bodily fluids. Accordingly, the fluids may present a source or nidus for harmful microbes, such as bacteria, fungi, viruses, or the like. By providing an antimicrobial material on one or more portions of the fluid impermeable barrier, the wicking material, or the conduit, the microbial (e.g., bacterial, fungal, etc.) growth is limited or stopped, thereby limiting or preventing the onset of infection and production of odors.

The fluid collection devices disclosed herein are configured to be used in fluid collection systems to collect and remove fluids from the wearer of the fluid collection device.

Figure 1A:
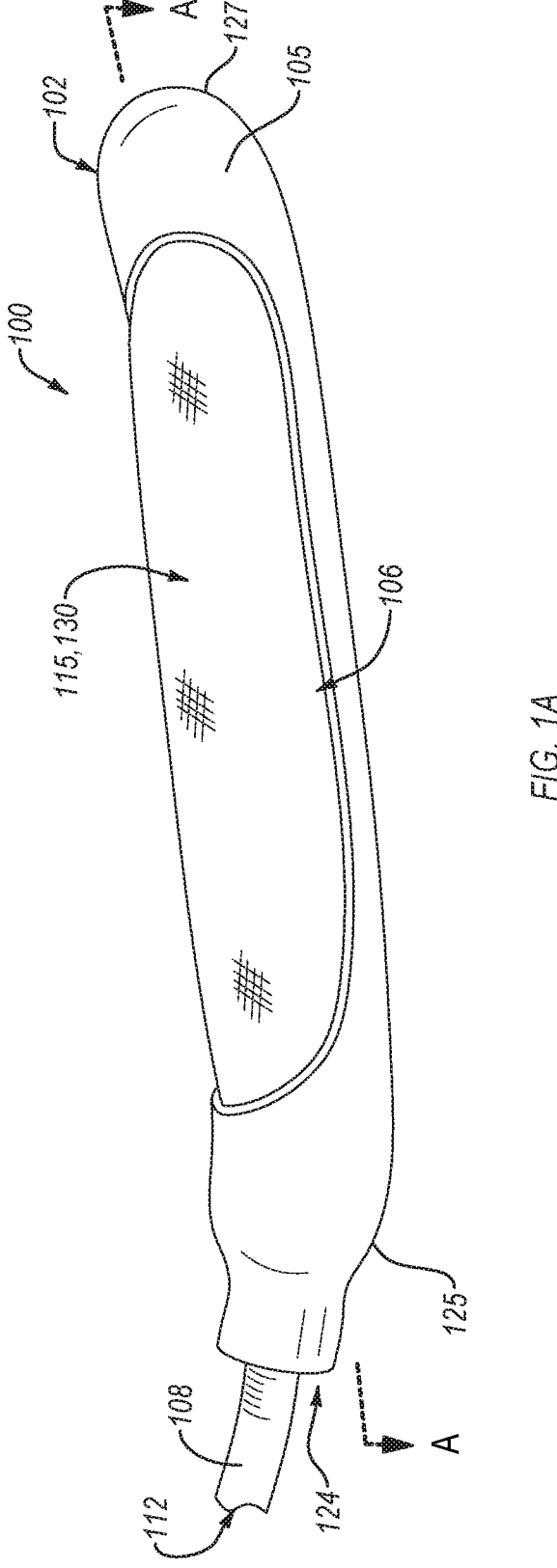
FIG. 1A is an isometric view of a fluid collection device, according to an embodiment.
Figure 1B:
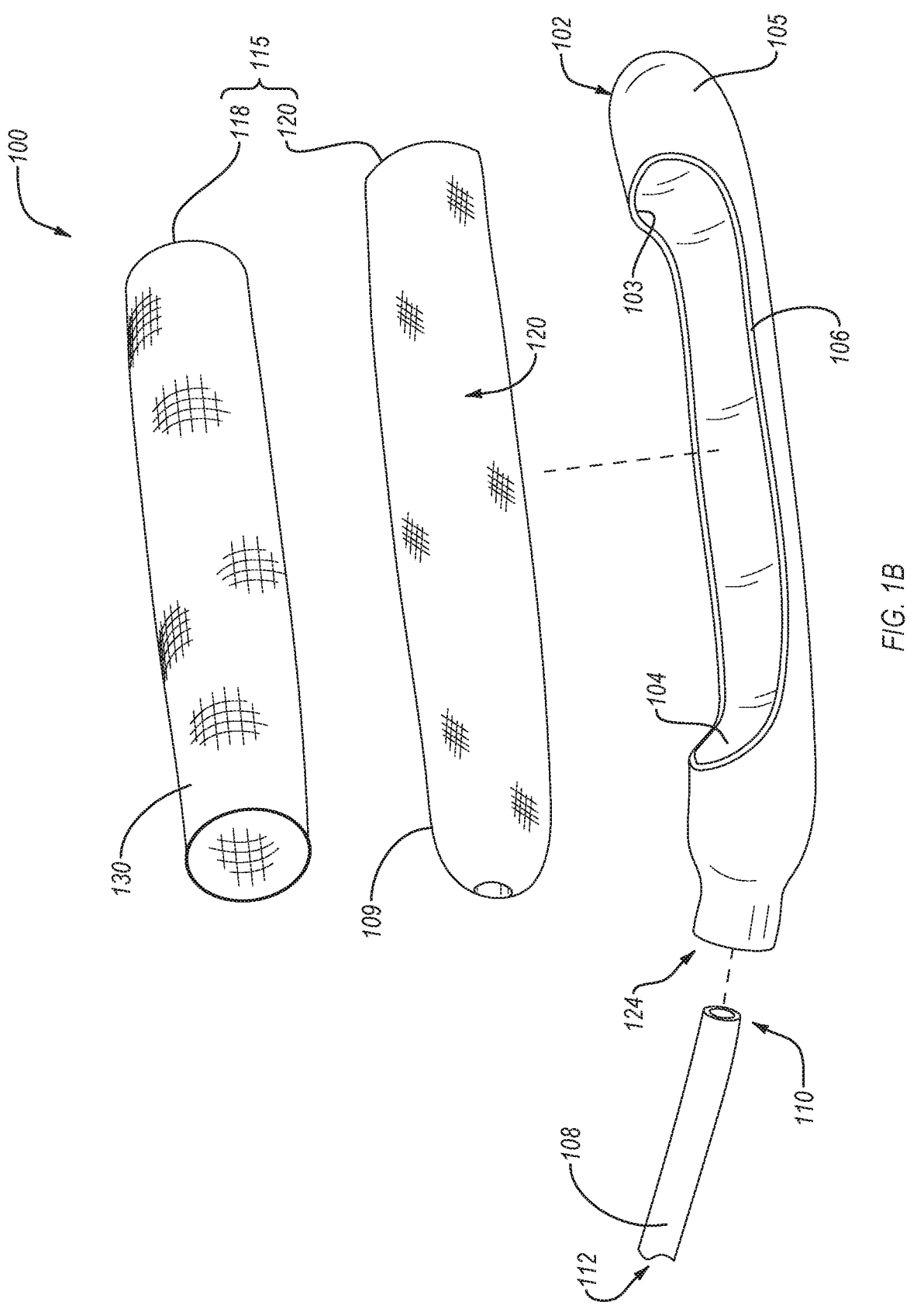
FIG. 1B is an exploded view of the fluid collection device of FIG. 1A.

FIG. 1A is an isometric view of a fluid collection device 100, according to an embodiment. FIG. 1B is an exploded view of the fluid collection device 100 of FIG. 1A. The fluid collection device 100 is an example of a female fluid collection device for receiving and collecting fluid(s) from a female. The fluid collection device 100 includes a fluid impermeable barrier 102, wicking material 115 disposed in a chamber within the fluid impermeable barrier 102, an antimicrobial material 130, and an optional conduit 108 at least partially disposed within the chamber.

The fluid impermeable barrier 102 at least partially defines a chamber 104 (e.g., interior region) and an opening 106. For example, the interior surface(s) 103 of the fluid impermeable barrier 102 at least partially define the chamber 104 within the fluid collection device 100. The fluid impermeable barrier 102 at least temporarily retains the fluid(s) in the chamber 104. The fluid impermeable barrier 102 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. As such, the fluid impermeable barrier 102 substantially prevents the fluid(s) from passing through the fluid impermeable barrier 102.

In some examples, the fluid impermeable barrier 102 may be tubular (ignoring the opening), such as substantially cylindrical (as shown), oblong, prismatic, or flattened tubes. The fluid impermeable barrier 102 may be sized to fit between the legs of a female user. During use, the outer surface 105 of the fluid impermeable barrier 102 may contact the wearer.

The opening 106 provides an ingress route for fluids to enter the chamber 104. The opening 106 may be defined by the fluid impermeable barrier 102, such as by an inner edge of the fluid impermeable barrier 102. For example, the opening 106 is formed in and extends through the fluid impermeable barrier 102, from the outer surface 105 to the inner surface 103, thereby enabling fluid(s) to enter the chamber 104 from outside of the fluid collection device 100. The opening 106 may be located and shaped to be positioned adjacent to a female urethra. At least a portion of wicking material(s) disposed in the chamber 104 may be exposed through the opening 106, to wick fluids inwardly into the chamber 104.

The fluid collection device 100 may be positioned proximate to the female urethra and urine may enter the chamber 104 via the opening 106. When in use, the opening 106 may be an elongated shape that extends from a first location below the urethral opening (e.g., at or near the anus or the vaginal opening) to a second location above the urethral opening (e.g., at or near the top of the vaginal opening or the pubic region).

The opening 106 may exhibit an elongated shape because the space between the legs of a female is relatively small when the legs of the female are closed, thereby only permitting the flow of the fluid(s) along a path that corresponds to the elongated shape of the opening 106 (e.g., longitudinally extending opening). The opening 106 in the fluid impermeable barrier 102 may exhibit a length that is measured along the longitudinal axis of the fluid collection device 100 that may be at least about 10% of the length of the fluid collection device 100, such as about 25% to about 50%, about 40% to about 60%, about 50% to about 75%, about 65% to about 85%, or about 75% to about 95% of the length of the fluid collection device 100.

The opening 106 in the fluid impermeable barrier 102 may exhibit a width that is measured transverse to the longitudinal axis of the fluid collection device 100 that may be at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 may exhibit a width that is greater than 50% of the circumference of the fluid collection device 100 since the vacuum (e.g., suction) through the conduit 108 pulls the fluid through the wicking material 115 and into the conduit 108. In some examples, the opening 106 may be vertically oriented (e.g., having a major axis parallel to the longitudinal axis of the device 100). In some examples (not shown), the opening 106 may be horizontally oriented (e.g., having a major axis perpendicular to the longitudinal axis of the device 100). In an example, the fluid impermeable barrier 102 may be attached to the individual, such as adhesively attached (e.g., with a hydrogel adhesive) to the individual. According to an example, a suitable adhesive is a hydrogel layer.

The fluid collection device 100 includes wicking material 115 disposed in the chamber 104. The wicking material 115 may cover at least a portion (e.g., all) of the opening 106. For example, at least a portion of the wicking material 115 may be exposed to an environment outside of the chamber 104 through the opening 106. The wicking material 115 may be configured to wick any fluid away from the opening 106, thereby preventing the fluid from escaping the chamber 104. The permeable properties referred to herein may be wicking, capillary action, diffusion, or other similar properties or processes, and are referred to herein as "permeable" and/or "wicking." Such "wicking" may not include absorption of fluid into the wicking material. Put another way, substantially no absorption of fluid into the material may take place after the material is exposed to the fluid and removed from the fluid for a time. While no absorption is desired, the term "substantially no absorption" may allow for nominal amounts of absorption of fluid into the wicking material (e.g., absorbency), such as less than about 10 wt % of the dry weight of the wicking material, less than about 7 wt %, less than about 5 wt %, less than about 3 wt %, less than about 2 wt %, less than about 1 wt %, or less than about 0.5 wt % of the dry weight of the wicking material. The wicking material 115 may also wick the fluid generally towards an interior of the chamber 104, as discussed in more detail below. The wicking material 115 may include one or more of a fluid permeable membrane 118 or a fluid permeable support 120.

The fluid permeable membrane 118 may include any material that may wick the fluid. For example, the fluid permeable membrane 118 may include fabric, such as a gauze (e.g., a silk, linen, or cotton gauze), another soft fabric, or another smooth fabric. The fluid permeable membrane 118 may include spun plastic fibers, such as a spun plastic mat or bed. Forming the fluid permeable membrane 118 from gauze, soft fabric, and/or smooth fabric may reduce chaffing caused by the fluid collection device 100.

The fluid collection device 100 may include the fluid permeable membrane 118 disposed in the chamber 104. The fluid permeable membrane 118 may cover at least a portion (e.g., all) of the opening 106. The fluid permeable membrane 118 may composed to wick any fluid away from the opening 106, thereby preventing the fluid from escaping the chamber 104.

The fluid collection device 100 may include the fluid permeable support 120 disposed in the chamber 104. The fluid permeable support 120 is configured to support the fluid permeable membrane 118 since the fluid permeable membrane 118 may be formed from a foldable, flimsy, or otherwise easily deformable material. For example, the fluid permeable support 120 may be positioned such that the fluid permeable membrane 118 is disposed between the fluid permeable support 120 and the fluid impermeable barrier 102. As such, the fluid permeable support 120 may support and maintain the position of the fluid permeable membrane 118. The fluid permeable support 120 may include any material that may wick the fluid, such as any of the fluid permeable membrane materials disclosed herein. For example, the fluid permeable membrane material(s) may be utilized in a more dense or rigid form than in the fluid permeable membrane 118 when used as the fluid permeable support 120. The fluid permeable support 120 may be formed from any fluid permeable material that is less deformable than the fluid permeable membrane 118, such as any of the materials disclosed herein for the fluid permeable membrane 118, in a more dense or rigid form. For example, the fluid permeable support 120 may include a porous polymer (e.g., nylon, polyester, polyurethane, polyethylene, polypropylene, etc.) structure or an open cell foam or spun plastic fibers. In some examples, the fluid permeable support 120 may be formed from a natural material, such as cotton, wool, silk, or combinations thereof. In such examples, the material may have a coating to prevent or limit absorption of fluid into the material, such as a water repellent coating. In some examples, the fluid permeable support 120 may be formed from fabric, felt, gauze, or combinations thereof. In some examples, the fluid permeable support 120 may be omitted from the fluid collection device 100. In some examples, the fluid permeable membrane 118 may be optional. For example, the wicking material 115 may include only the fluid permeable support 120.

The fluid permeable support 120 may have a greater ability to wick fluids than the fluid permeable membrane 118, such as to move the fluid inwardly from the outer surface of the fluid collection device 100. In some examples, the wicking ability of the fluid permeable support 120 and the fluid permeable membrane 118 may be substantially the same.

The fluid permeable membrane 118 and the fluid permeable support 120 may at least substantially completely fill the portions of the chamber 104 that are not occupied by the conduit 108. In another example, the fluid permeable membrane 118 and the fluid permeable support 120 may not substantially completely fill the portions of the chamber 104 that are not occupied by the conduit 108. In such an example, the fluid collection device 100 includes the reservoir (FIG. 1C) in the chamber 104.

The fluid collection device 100 includes the conduit 108, which extends into the chamber 104. The fluid collection device 100 may be operably coupled to a vacuum source. Accordingly, fluids may be removed from the chamber 104 via the conduit 108. The conduit 108 may extend into the chamber 104 to any point therein. For example, the conduit 108 may be inserted into the chamber at the first end region 125 of the fluid collection device 100 and extend therethrough to the second end region 127 of the fluid collection device 100.

The fluid impermeable barrier 102, the fluid permeable membrane 118 and the fluid permeable support 120 may be configured to have the conduit 108 at least partially disposed in the chamber 104. For example, at least one of the fluid permeable membrane 118 and the fluid permeable support 120 may be configured to form a space that accommodates the conduit 108. The fluid impermeable barrier 102 may define an aperture sized to receive the conduit 108. The at least one conduit 108 may be disposed in the chamber 104 via the aperture. The apertures may be configured to form an at least substantially fluid tight seal against the conduit 108 or the at least one tube thereby substantially preventing the fluid(s) from escaping the chamber 104. The fluid collected in the fluid collection device 100 may be removed from the chamber 104 via the conduit 108.

The fluid collection devices 100 disclosed herein include antimicrobial material 130 therein. The antimicrobial material 130 may be carried by one or more of the fluid impermeable barrier 102 or the wicking material 115. For example, antimicrobial material 130 may be disposed on, in, or incorporated into any of the fluid impermeable barrier 102, fluid permeable membrane 118, fluid permeable support 120, or the conduit 108, in one or more locations thereof.

The antimicrobial material may include one or more of an antibiotic material or an antifungal material. The antimicrobial material may include one or more of an antimicrobial organic compound, an inorganic compound, a polymeric biocidal or fungicidal material, metals, or any other material which reduces or prevents bacterial or fungal cell growth. Exemplary antimicrobial organic compounds may include organic acid salts, halogenated (e.g., chlorinated) polymers, nitrofurazone, organosilanes, or the like. Antimicrobial metals may include one or more of silver, titanium, cobalt, nickel, copper, brass, bronze, gold, zinc, zirconium, molybdenum, or tin. The antimicrobial material may include an oxide (e.g., zinc oxide), halide (e.g., chloride, bromide, iodide, etc.), sulfate, or another salt of any of the foregoing metals. The antimicrobial polymeric biocide may include polyhexamethylene guanidine hydrochloride (PHMGH), low density polyethylene (LDPE), nylon-3 polymers, polyethylene glycol(s), polymers containing phosphonium salts, ammonium salts, phenol groups, halogen-containing salts, or the like. Example antimicrobial inorganic materials may include sodium bicarbonate or the like As shown in FIGS. 1A and 1B, the antimicrobial material 130 may be incorporated into the wicking material 115, such as in the fluid permeable membrane 118. In some examples, the antimicrobial material 130 may be coated onto or impregnated in the fluid permeable membrane 118, the fluid permeable support 120, the fluid impermeable barrier 102, or the conduit 108. For example, one or both of the fluid permeable membrane 118 or fluid permeable support 120 may include fibers incorporating the antimicrobial material 130. In some examples, natural or synthetic fibers or a foam of the wicking material 115 may be coated with the antimicrobial material 130.

The antimicrobial material 130 may be woven into the wicking material 115, such as in the fluid permeable membrane 118 or the fluid permeable support 120. The antimicrobial material 130 may be disposed in or on threads in the fluid permeable membrane 118. For example, particles of silver, copper, aluminum, or another antimicrobial material may be disposed in the fibers or threads. In some examples, the antimicrobial fibers or threads may be present as less than 50% of the fibers or threads in the fluid permeable membrane 118, such as 1% to 50%, 1% to 10%, 5% to 25%, or 25% to 50% of the fibers or threads in the fluid permeable membrane 118. In some examples, the antimicrobial fibers or threads may be present as more than 50% of the fibers or threads in the fluid permeable membrane 118, such as in all of the threads of the fluid permeable membrane 118. In some examples, the antimicrobial material 130 may be coated onto the fibers or threads.

In some examples, the fibers or threads may be at least partially made of biocidal polymeric material. In some examples, the fibers or threads may be, or include, a wire of any of the antimicrobial materials disclosed herein.

In some examples, the antimicrobial material may be incorporated into the fluid impermeable barrier 102. For example, a polymer fluid impermeable barrier may include antimicrobial particles dispersed therein, such as any of the metals, polymers, or other antimicrobial materials disclosed herein. In some examples, antimicrobial material(s) may be less than 50 weight percent (wt %) of the fluid impermeable barrier 102, such as 0.1 wt % to 50 wt %, 0.1 wt % to 5 wt %, 1 wt % to 10 wt %, 10 wt % to 25 wt %, 20 wt % to 40 wt %, 25 wt % to 50 wt %, less than 25 wt %, less than 10 wt %, or more than 0.1 wt % of the fluid impermeable barrier 102.

As explained in more detail below, the antimicrobial material may be disposed on one or more surfaces of the fluid impermeable barrier 102, the wicking material 115, or the conduit 108. For example, the antimicrobial material may be disposed on one or more portions of at least one of the inner surface or the outer surface of the fluid impermeable barrier 102. In some examples, the antimicrobial material may be disposed in the wicking material as a powder applied thereto or may be coated thereon.

The conduit 108 may be at least partially disposed in the chamber 104. The conduit 108 (e.g., a tube) includes an inlet 110 at a first end region and an outlet 112 at a second end region positioned downstream from the inlet 110. The conduit 108 fluidly couples an interior region of the chamber 104 with the fluid storage container (not shown) or the vacuum source (not shown). The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 108 may include silicon or latex. In some examples, the conduit 108 may include one or more portions that are resilient, such as to by having one or more of a diameter or wall thickness that allows the conduit to be flexible.

In the illustrated embodiment of FIG. 1B, the conduit 108 is at least partially disposed in the chamber 104. For example, the conduit 108 may extend into the fluid impermeable barrier 102 from the first end region (e.g., proximate to the outlet 112) and may extend to the second end region (e.g., opposite the first end region) to a point proximate to a reservoir therein such that the inlet 110 is in fluid communication with the reservoir. In some examples (not shown), the conduit 108 may enter the chamber 104 in the second end region and the inlet 110 of the conduit 108 may be disposed in the second end region (e.g., in the reservoir). The fluid collected in the fluid collection device 100 may be removed from the chamber 104 via the conduit 108.

Figure 1C:
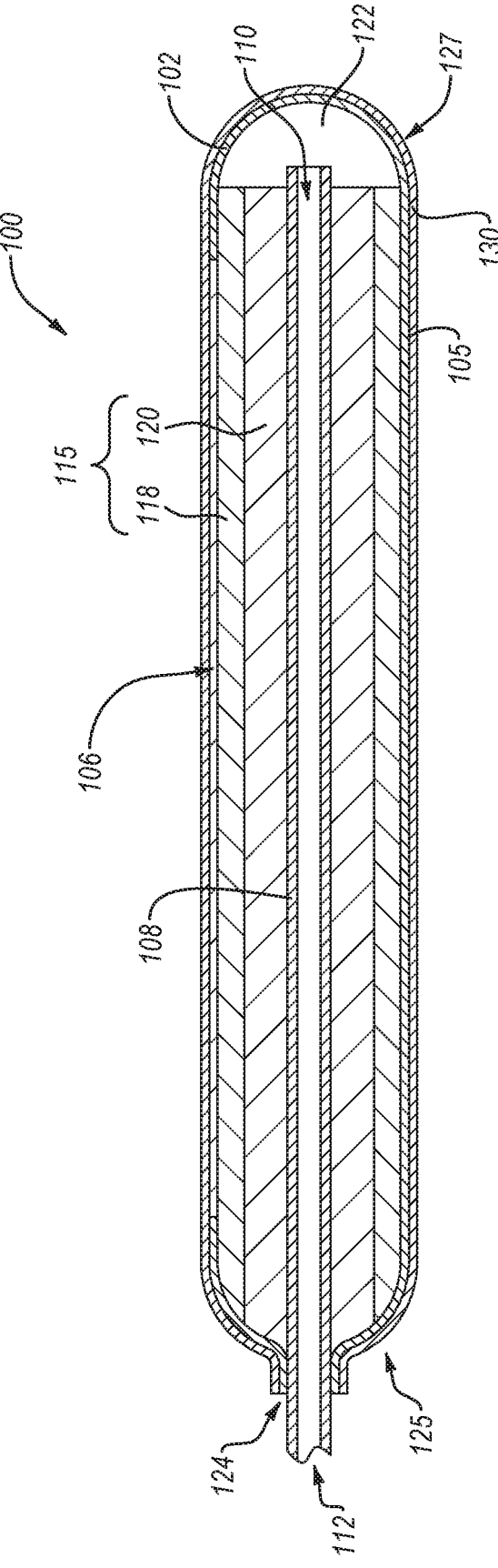
FIG. 1C is a cross-sectional view of the fluid collection device of FIG. 1A taken along the plane A-A, according to an embodiment.

In some examples, the antimicrobial material 130 may be disposed on an outermost surface of the fluid collection device, such as one or more portions expected to be in contact with a wearer when in use. In some examples, the fluid collection device may include a reservoir therein. FIG. 1C is a cross-sectional view of the fluid collection device of FIG. 1A taken along the plane A-A, according to an embodiment. FIG. 1C depicts the fluid collection device 100c. The fluid collection device 100c includes the fluid impermeable barrier 102, the wicking material 115, the conduit 108, and the antimicrobial material 130 disposed on an outer surface of the fluid impermeable barrier 102 and the outer surface of the wicking material 115.

The antimicrobial material 130 may be disposed on one or more portions of at least one of the outer surface or the inner surface of the fluid impermeable barrier 102. In some examples, the antimicrobial material 130 may be incorporated into, or carried on, a material disposed on an outer surface of the fluid impermeable barrier 102. The antimicrobial material 130 may be disposed on the fluid collection device 100c as a coating on one or more portions thereof. The coating may include a carrier having a layer of antimicrobial material thereon or incorporating antimicrobial particles therein, such as a polymer having metal particles or nitrofurazone therein. The thickness of the antimicrobial material (e.g., coating) may be less than 1 mm, such as 1 μm to 1 mm, 1 μm to 10 mm, 1 μm to 10 μm, 10 μm to 100 μm, 100 μm to 500 μm, less than 500 μm, or less than 100 μm.

By disposing the antimicrobial material on the outer surface(s) of the fluid collection device 100c, bacterial and/or fungal growth may be reduced or eliminated while the fluid collection device 100c is in use. Accordingly, infections and odors may be reduced or eliminated compared to conventional fluid collection devices, particularly at points where the fluid collection device comes into contact with the wearer. Disposing the antimicrobial material on the portions of the fluid collection device may also aid in preventing the transfer of bacterial or fungal infections from the device to the wearer or vice versa.

While shown as being disposed on substantially the entire outer surface of the fluid collection device 100c, in some examples the antimicrobial material may only be disposed on an upper surface (e.g., portions of the fluid collection device at and around the opening 106) of the fluid collection device. For example, the antimicrobial material 130 may only be disposed on portions of the outer surface expected to be in contact with the user.

In some examples, the antimicrobial material 130 may be incorporated into or carried on a compression material disposed on the outer surface of the fluid impermeable barrier 102. For example, a compression bandage may have antimicrobial materials incorporated therein, such as having embedded antimicrobial polymer or metal particles or antimicrobial fibers. The compression bandage may have silver, copper, or aluminum particles or fibers therein. The compression bandage may be used to form an antimicrobial coating over one or more portions (e.g., cover the entire outer surface) of the fluid collection device 100*c* or may be utilized as the fluid permeable membrane 118. Suitable compression bandages may include natural and/or synthetic fibers therein, such as cotton, spandex, lycra, etc.

The antimicrobial material 130 may be located on one or more portions of the interior surface of the fluid impermeable barrier 102. By disposing the antimicrobial material on the interior surface of the fluid impermeable barrier 102, odors and microbial growth in the fluids collected therein may be reduced or eliminated.

In some examples, the antimicrobial material may be coated on or incorporated into the conduit 108. For example, a polymer conduit may include antimicrobial particles dispersed therein, such as any of the metals, polymers, or other antimicrobial materials disclosed herein. In some examples, antimicrobial material(s) may be less than 50 weight percent (wt %) of the conduit, such as 0.1 wt % to 50 wt %, 0.1 wt % to 5 wt %, 1 wt % to 10 wt %, 10 wt % to 25 wt %, 20 wt % to 40 wt %, 25 wt % to 50 wt %, less than 25 wt %, less than 10 wt %, or more than 0.1 wt % of the conduit. In some examples, the antimicrobial material may be coated onto one or more of an outer surface or an inner surface of the conduit 108. In such examples, bacterial or fungal growth may be limited or eliminated on or in the conduit 108.

As shown in FIG. 1C, the end of the conduit 108 may extend to the fluid permeable membrane 118 and/or fluid permeable support 120, such as into a reservoir 122. For example, the inlet 110 may extend into or be positioned in the reservoir 122. As shown, the reservoir 122 is a substantially unoccupied portion of the chamber 104. The reservoir may be defined between the fluid impermeable barrier 102 and one or both of the fluid permeable membrane 118 and the fluid permeable support 120. The fluid(s) that are in the chamber 104 may flow through the fluid permeable membrane 118 and/or fluid permeable support 120 to the reservoir 122. The fluid impermeable barrier 102 may retain the fluid(s) in the reservoir 122. While depicted in the second end region 127, the reservoir 122 may be located in any portion of the chamber 104 such as the first end region 125. In an example, the fluid impermeable barrier 102 may be air permeable and liquid impermeable. In such an example, the fluid impermeable barrier 102 may be formed of a hydrophobic material that defines a plurality of pores that are air permeable but not liquid permeable. In an example, at least one or more portions of at least an outer surface of the fluid impermeable barrier 102 may be formed from a soft and/or smooth material, thereby reducing chaffing.

In some examples, the inlet 110 may not extend into the reservoir 122. In such examples, the inlet 110 may be disposed within the wicking material 115 (fluid permeable membrane 118 and/or fluid permeable support 120) or at a terminal end thereof. For example, an end of the conduit 108 may be coextensive with or recessed within the fluid permeable membrane 118 and/or fluid permeable support 120.

In another example, the fluid permeable membrane 118 and the fluid permeable support 120 may not substantially completely fill the portions of the chamber 104 that are not occupied by the conduit 108. In such an example, the fluid collection device 100 includes the reservoir 122 disposed in the chamber 104. The reservoir 122 is a substantially unoccupied portion of the chamber 104. The reservoir may be defined between the fluid impermeable barrier 102 and one or both of the fluid permeable membrane 118 and the fluid permeable support. The fluid(s) that are in the chamber 104 may flow through the fluid permeable membrane 118 and/or fluid permeable support 120 to the reservoir 122. For example, the reservoir 122 may be located in a portion of the fluid collection device expected to be positioned in a gravimetrically low point of the fluid collection device when worn by a user. The reservoir 122 may store at least some of the fluid(s) therein.

In some examples, the fluid collection device 100 may include multiple reservoirs, such as a first reservoir that is located at the portion of the chamber 104 closest to the inlet 110 (e.g., second end region 127) and a second reservoir that is located at the portion of the of the chamber 104 that is closest to the outlet 112 (e.g., first end region 125). In another example, the fluid permeable support 120 is spaced from at least a portion of the conduit 108 and the reservoir 122 may be the space between the fluid permeable support 120 and the conduit 108.

The fluid impermeable barrier 102, the fluid permeable membrane 118 and the fluid permeable support 120 may be configured to have the conduit 108 at least partially disposed in the chamber 104. For example, at least one of the fluid permeable membrane 118 and the fluid permeable support 120 may be configured to form a space that accommodates the conduit 108. In another example, the fluid impermeable barrier 102 may define an aperture 124 sized to receive the conduit 108 (e.g., at least one tube). The at least one conduit 108 may be disposed in the chamber 104 via the aperture 124. The aperture 124 may be configured to form an at least substantially fluid tight seal against the conduit 108 thereby substantially preventing the fluid(s) from escaping the chamber 104. The fluid collected in the fluid collection device 100 may be removed from the interior region of the chamber 104 via the conduit 108. As shown in FIG. 1C, the end of the conduit 108 may extend beyond the fluid permeable membrane 118 and/or fluid permeable support 120, such as into the reservoir 122. In some examples, the inlet 110 may not extend into the reservoir 122. In such examples, the inlet 110 may be disposed within the wicking material (fluid permeable membrane 118 and/or fluid permeable support 120) or a terminal end thereof. For example, an end of the conduit 108 may be coextensive with or recessed within the fluid permeable membrane 118 and/or fluid permeable support 120.

Locating the inlet 110 at or near a location expected to be the gravimetrically low point of the chamber 104 when worn by a user enables the conduit 108 to receive more of the fluid(s) than if inlet 110 was located elsewhere and reduce the likelihood of pooling (e.g., pooling of the fluid(s) may cause microbe growth and foul odors). For instance, the fluid(s) in the fluid permeable membrane 118 and the fluid permeable support 120 may flow in any direction due to capillary forces. However, the fluid(s) may exhibit a preference to flow in the direction of gravity, especially when at least a portion of the fluid permeable membrane 118 and/or the fluid permeable support 120 is saturated with the fluid(s). Accordingly, one or more of the inlet 110 or the reservoir 122 may be located in the second end region 127.

In an example, the conduit 108 is configured to be at least insertable into the chamber 104. In such an example, the conduit 108 may include one or more markers (not shown) on an exterior thereof that are configure to facilitate insertion of the conduit 108 into the chamber 104. For example, the conduit 108 may include one or more markings thereon that are configured to prevent over or under insertion of the conduit 108, such as when the conduit 108 defines an inlet 110 that is configured to be disposed in or adjacent to the reservoir 122. In another example, the conduit 108 may include one or more markings thereon that are configured to facilitate correct rotation of the conduit 108 relative to the chamber 104. In an example, the one or more markings may include a line, a dot, a sticker, or any other suitable marking.

The fluid impermeable barrier 102 may include markings thereon, such as one or more markings to aid a user in aligning the device 100 on the wearer. For example, a line on the fluid impermeable barrier 102 (e.g., opposite the opening 106) may allow a healthcare professional to align the opening 106 over the urethra of the wearer. In examples, the markings may include one or more of an alignment guide or an orientation indicator, such as a stripe or hashes. Such markings may be positioned to align the device 100 to one or more anatomical features such as a pubic bone, etc.

Other embodiments of fluid impermeable barriers, fluid permeable membranes, fluid permeable supports, chambers, and their shapes and configurations are disclosed in U.S. patent application Ser. No. 15/612,325 filed on Jun. 2, 2017; U.S. Pat. No. 10,390,989 filed on Sep. 8, 2016; and U.S. Pat. No. 10,226,376 filed on Jun. 1, 2017, the disclosure of each of which is incorporated herein, in its entirety, by this reference.

In an example, one or more components (e.g., fluid impermeable barrier 102, conduit 108, the wicking material 115, etc.) of the fluid collection device 100 may include an odor blocking or absorbing material such as a cyclodextrine-containing material or a thermoplastic elastomer (TPE) polymer.

As described in more detail below, the conduit 108 is configured to be coupled to and at least partially extend between one or more of the fluid storage container (not shown) and the vacuum source (not shown). In an example, the conduit 108 is configured to be directly connected to the vacuum source (not shown). In such an example, the conduit 108 may extend from the fluid impermeable barrier 102 by at least one foot, at least two feet, at least three feet, or at least six feet. In another example, the conduit 108 may be indirectly connected to at least one of the fluid storage container (not shown) and the vacuum source (not shown). In some examples, the conduit is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 110 and the outlet 112 may fluidly couple (e.g., directly or indirectly) the vacuum source (not shown) to the chamber 104 (e.g., the reservoir 122), such as via one or more connectors thereon. In an example, the inlet 110 and/or the outlet 112 may form a male connector. In another example, the inlet 110 and/or the outlet 112 may form a female connector. In an example, the inlet 110 and/or the outlet 112 may include ribs that are configured to facilitate secure couplings. In an example, the inlet 110 and/or the outlet 112 form a tapered shape. In an example, the inlet 110 and/or the outlet 112 may include a rigid or flexible material.

As the vacuum source (FIG. 3) applies a vacuum/suction in the conduit 108, the fluid(s) in the chamber 104 (e.g., at the second end region such as in the reservoir 122) are drawn into the inlet 110 and out of the fluid collection device 100 via the conduit 108. In some examples, the conduit may be frosted or opaque (e.g., black) to obscure visibility of the fluid(s) therein.

The fluid collection devices shown in FIGS. 1A-1C are examples of female fluid collection devices that are configured to collect fluid(s) from females. However, the fluid collection devices, systems, and methods disclosed herein may include male fluid collection devices shaped, sized, and otherwise configured to collect fluid(s) from males.

Figure 2A:
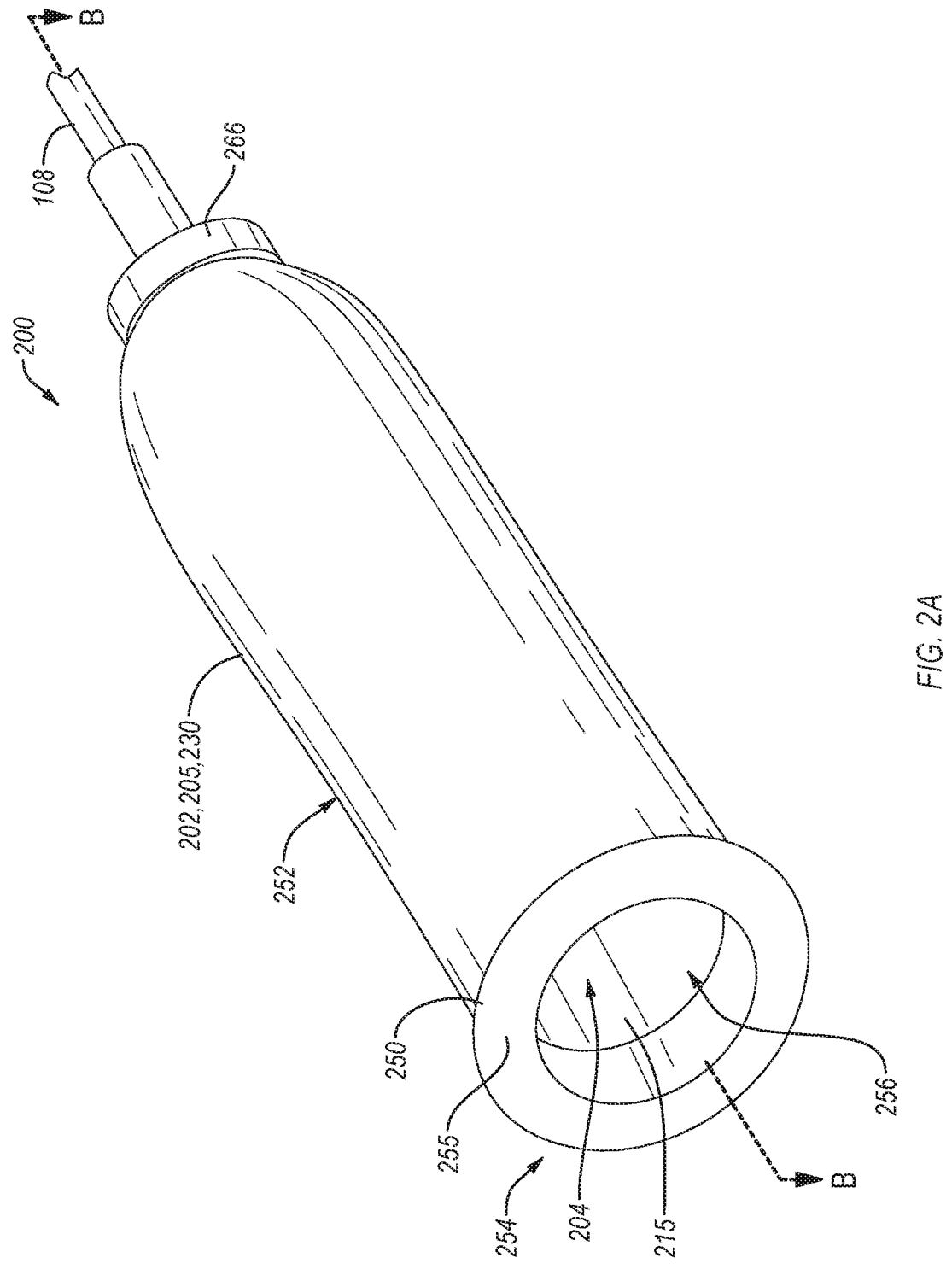
FIG. 2A is an isometric view of a fluid collection device, according to an embodiment.
Figure 2B:
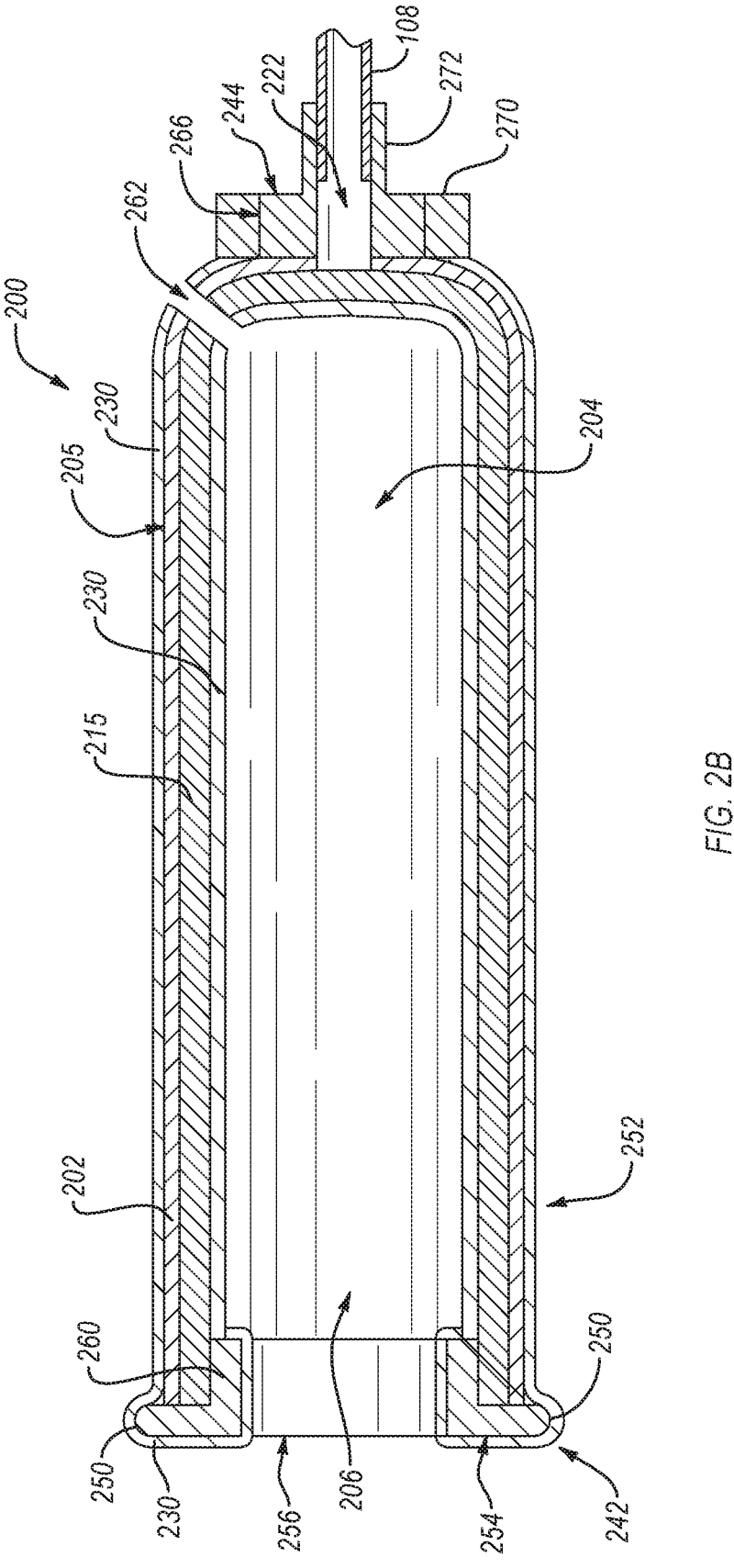
FIG. 2B is a cross-sectional view of a fluid collection device of FIG. 2A along the plane B-B, according to an embodiment.

FIG. 2A is an isometric view of a fluid collection device 200, according to an embodiment. FIG. 2B is a cross-sectional view of a fluid collection device 200 of FIG. 2A along the plane B-B, according to an embodiment. Referring to FIGS. 2A and 2B, the fluid collection device 200 includes a receptacle 250 and a sheath 252 (e.g., cup shaped container). The antimicrobial material 230 may be disposed on one or more surfaces of at least one of the receptacle 250 (including the wicking material disposed therein), the sheath 252, the cap 266, or the conduit 108. The antimicrobial material 230 may be similar or identical to the antimicrobial material 130 disclosed herein, in one or more aspects. For example, the antimicrobial material 230 may include one or more of an antimicrobial organic compound, an inorganic compound, a polymeric biocidal or fungicidal material, metals, or any other material which reduces or prevents bacterial or fungal cell growth as disclosed herein.

The receptacle 250 is sized, shaped, and made of a material to be coupled to skin that surrounds the male urethra and have the male urethra positioned therethrough. For example, the receptacle 250 may include an annular base 254 that defines an opening 256 in the receptacle 250. The annular base 254 is sized and shaped to be positioned around the male urethra (e.g., positioned around the penis) and the opening 256 may be configured to have the male urethra positioned therethrough. The annular base 254 may also be sized, shaped, made of a material, or otherwise configured to be coupled (e.g., adhesively attached, such as with a hydrogel adhesive) to around the male urethra (e.g., around the penis). In an example, the annular base 254 may exhibit the general shape of the skin surface that the annular base 254 is selected to be coupled with and/or may be flexible thereby allowing the annular base 254 to conform to any shape of the skin surface. The receptacle 250 also defines a hollowed region that is configured to receive (e.g., seal against) the sheath 252. For example, the receptacle 250 may include a flange 260 that extends upwardly from the annular base 254. The flange 260 may be tall enough to prevent the sheath 252 from being accidentally removed from the receptacle 250 (e.g., at least 0.5 cm tall, 1 cm tall, at least 2 cm tall, or at least 5 cm tall). While depicted as being disposed within the sheath 252, in some examples the flange 260 may be disposed on the outer surface of the sheath 252.

The receptacle 250 may be formed of any of the materials disclosed herein for the fluid impermeable barrier 102, such as a silicone polymer.

In some examples, the antimicrobial material 230 may be disposed on one or more of the outer surface or the inner surface of the receptacle 250. The antimicrobial material 230 may be present as a coating, such as a coating of any of the antimicrobial materials disclosed herein. For example, the antimicrobial coating may be disposed on the annular base 254 or in the opening 256 where the fluid collection device 200 contacts the skin of a wearer, such as to prevent or limit growth or transmission of bacteria and fungi from the fluids to the wearer. The coating may include a carrier having antimicrobial particles therein, such as a polymer having metal particles or nitrofurazone therein. In some examples, the antimicrobial material 230 may be incorporated into the material of the receptacle 250, such as antimicrobial particles (e.g., metals) or polymers embedded in the receptacle material as disclosed herein with respect to the fluid impermeable barrier 102 of the fluid collection device 100. For example, the receptacle 250 may be formed of silicone having silver, copper, or aluminum impregnated therein.

The sheath 252 includes (e.g., may be formed from) a fluid impermeable barrier 202 that is sized and shaped to fit into or around opening 256 (e.g., the hollowed region) and/or flange 260 of the receptacle 250. The fluid impermeable barrier 202 may be disposed on wicking material 215. The wicking material 215 may be similar or identical to the wicking material 115 disclosed herein, in one or more aspects. For example, the wicking material 215 may include one or more of the fluid permeable membrane or the fluid permeable support as disclosed herein with respect to the wicking material 115. The fluid impermeable barrier 202 of the sheath 252 may be shaped to contain, and allow for, different sizes and states of male penises. For example, the sheath 252 may be generally cup-shaped or tubular with a substantially closed end. For example, the sheath 252 may be substantially cylindrical with a closed distal end. The cylindrical sheath 252 may be substantially cylindrical in that the cylinder may be deformable and at least partially collapsible/expandable based on the size and state of the penis of the wearer. Accordingly, the penis of a wearer may be inserted into and contained within the sheath 252 whether in a flaccid or erect state.

The fluid impermeable barrier 202 may be similar or identical to the fluid impermeable barrier 102, in one or more aspects such as material composition, thickness, fluid retention, etc. The fluid impermeable barrier 202 at least partially defines a chamber 204 therein. The fluid impermeable barrier 202 may also define an opening 206 extending through the fluid impermeable barrier 202 to the chamber 204.

In some examples, the antimicrobial material 230 may be disposed on one or more of the outer surface or the inner surface of the fluid impermeable barrier 202. The antimicrobial material 230 may be present as a coating, such as any of the coatings disclosed herein. In some examples, the antimicrobial material 230 may be incorporated into the fluid impermeable barrier, such as disclosed herein with respect to the fluid collection device 100.

The fluid impermeable barrier 202 may also include at least one aperture 262 that allows the chamber 204 to remain substantially at atmospheric pressure even when suction or a vacuum is applied in the chamber 204. The aperture 262 may be located on any portion of the sheath 252, such as a portion not intended to serve as a reservoir for collected fluids. In some examples (not shown), the aperture 262 may extend through the cap 266 or be disposed beneath the cap 266. In some examples, the fluid collection device 200 may not include the aperture 262, such as when a more complete seal as desired for the chamber 204.

The fluid impermeable barrier 202 may have the wicking material 215 in an inner surface thereof to form a fluid impermeable barrier separating the interior (e.g., chamber 204) of the fluid collection device 200 from the external environment. One or more of the fluid permeable membrane or the fluid permeable support may extend around at least a portion of the inner surface of the fluid impermeable barrier 202. In some examples, the fluid permeable membrane or the fluid permeable support may be omitted from the wicking material 215. One or more portions of the fluid impermeable barrier 202 may be adhered to the outer surface of the wicking material 215 (e.g., the fluid permeable membrane or the fluid permeable support). Put another way, the fluid permeable support may be disposed on an interior surface of the fluid impermeable barrier 202. The fluid permeable membrane may be disposed on an interior surface of the fluid permeable support, such as disposed concentrically within the fluid permeable support. In such examples, the fluid permeable membrane may contact the skin of the wearer (e.g., penis) when in use. In some examples (not shown), the fluid permeable membrane may be located at the outer surface of the wicking material 215, wherein the fluid impermeable barrier 202 is adhered to the outer surface of the fluid permeable membrane.

The antimicrobial material 230 may be located on or incorporated into the wicking material 215 as disclosed with respect to the fluid collection device 100. For example, the antimicrobial material may include fibers or threads bearing antimicrobial material (e.g., silver or copper) therein. As shown in FIG. 2B, the antimicrobial material 230 may be a coating applied to the innermost surface of the wicking material 215.

To facilitate fluid collection and provide comfort, the sheath 252 may be flexible, relatively soft, and have a relatively smooth outer surface, thereby allowing the sheath 252 to correspond to the shape of a penis. For example, the sheath 252 may at least partially collapse when the penis is flaccid and at least partially expand and bend to the shape of the penis as the penis becomes erect.

The receptacle 250 may be more rigid than the sheath 252. For example, the receptacle 250 may be formed from a flexible polymer that is at least one of thicker than the entire sheath 252 or exhibits a Young's modulus that is greater than sheath 252. As such, the receptacle 250 may provide some structure at or near the proximal end 242 of the fluid collection device 200. The higher rigidity of the receptacle 250 may cause the receptacle 250 to remain open, thereby facilitating insertion of the urethra (e.g., penis) into the fluid collection device 200. The relatively high rigidity of the receptacle 250 enables the receptacle 250 to act as an attachment point to a wearer, wicking material 215, and/or the fluid impermeable barrier 202. In some examples, the receptacle 250 may define a recess, include threads, or include any other attachment substrate for attaching the components of the fluid collection device 200, such as the wicking material 215 or the fluid impermeable barrier 202.

In some examples, the fluid collection device 200 includes a cap 266 at a distal end region 244. The cap 266 defines a in interior channel through which the fluids may be removed from the fluid collection device 200. The interior channel is in fluid communication with the chamber 204. The cap 266 may be disposed over at least a portion of the distal end region 244 of one or more of the fluid impermeable barrier 202 or the wicking material 215. The cap 266 may be made of a polymer, rubber, or other fluid impermeable material. The cap 266 may be attached to one or more of the fluid impermeable barrier 202, the wicking material 215, or the conduit 108. The cap 266 may have a laterally extending flange 270 and a longitudinally extending flange 272. The laterally extending flange 270 may cover at least a portion of the distal end region 244 of the fluid collection device 200. The laterally extending flange 270 may extend laterally along the outer surface of the end of the sheath 252. The longitudinally extending flange 272 may extend a distance from the sheath 252. The longitudinally extending flange 272 is sized and configured to receive and fluidly seal against the conduit 108, such as within the interior channel The conduit 108 may extend a distance within the cap 266, such as to the wicking material 215, through the wicking material 215, or to a point set-off from the wicking material 215. In the latter example, as depicted in FIG. 2B, the interior channel of the cap 266 may define a reservoir 222 therein. The reservoir 222 is an unoccupied portion of the device such as in the cap 266 and is void of other material. In some examples, the reservoir 222 is defined at least partially by the wicking material 215 and the cap 266. During use, the fluids that are in the chamber 204 may flow through the wicking material 215 to the reservoir 222. The reservoir 222 may store at least some of the fluids therein and/or position the fluids for removal by the conduit 108. In some examples, at least a portion of the wicking material 215 may extend continuously between at least a portion of the opening of the interior channel and chamber 204 to wick any fluid from the opening directly to the reservoir 222. In some examples, the reservoir may be defined between the interior surface of the fluid impermeable barrier and the penis of a wearer, such as an unoccupied portion of the chamber 204.

In some examples (not shown), the fluid impermeable barrier 202 may be disposed on the cap 266, such as enclosing the cap 266 within the chamber 204.

In some examples, the sheath 252 may include at least a portion of the conduit 108 therein, such as at least partially disposed in the chamber 204. For example, the conduit 108 may extend from the sheath 252 to a region at least proximate to the opening 256. For example, the inlet of the conduit may be positioned adjacent to the annular base 254. The region proximate to the opening 256 may be disposed near or on the skin around the male urethra (e.g., around the penis). Accordingly, when a patient lays on their back, fluid (e.g., urine) may aggregate near the opening 206 against the skin of the wearer. The fluid may be removed from the chamber 204 via the conduit 108. The conduit 108 includes the inlet positioned within the fluid collection device and an outlet configured to be fluidly coupled to a vacuum source. The antimicrobial material 230 may be disposed on the outer surface, inner surface, or incorporated into, the material of the conduit 108.

The receptacle 250, the sheath 252, the cap 266, and the conduit 108 may be attached together using any suitable method. For example, at least two of the receptacle 250, the sheath 252, the cap 266, or the conduit 108 may be attached together using at least one of an interference fit, an adhesive, stitching, welding (e.g., ultrasonic welding), tape, any other suitable method, or combinations thereof. The antimicrobial material may be located on one or more portions of the receptacle, the sheath, the cap, or the conduit.

In some examples, the vacuum source (not shown) may be remotely located from the sheath 252. In such examples, the conduit 108 may extend out of and away from the sheath 252 to the vacuum source or a fluid storage container. For example, the inlet 110 of the conduit may be used to remove fluid from the chamber 204 via vacuum when an outlet (not shown) of the conduit 108 is fluidly coupled to the vacuum source or fluid storage container operably coupled to the vacuum source.

In some examples (not shown), the fluid collection device 200 does not include the cap. In such examples, the outlet of the conduit 108 may be fluidly coupled to a fluid storage container (not shown). In such examples, the fluid impermeable barrier 202 may include at least one aperture sized and shaped to receive and seal against the conduit 108, such as within the chamber 204. Accordingly, the chamber 204 may be fluidly coupled to the vacuum source via the conduit 108. As the vacuum source applies a vacuum/suction, the fluid in the chamber 204 may be removed through the conduit 108. In some examples, the fluid may be pumped through the vacuum source (not shown) into a section of the conduit 108 fluidly coupled to a fluid storage container (not shown) into which the fluid may be deposited.

In examples, portions of the chamber 204 may be substantially empty due to the varying sizes and rigidity of the male penis. However, in some examples (not shown), the outermost regions of the chamber 204 (e.g., periphery of the interior regions of the sheath 252) may include wicking material 215 in a position to blunt a stream of urine from the male urethra thereby limiting splashing and/or to direct the fluids to a selected region of the chamber 204. Since the chamber 204 is substantially empty (e.g., substantially all of the chamber 204 forms a reservoir), the fluids are likely to pool at a gravimetrically low point of the chamber 204. Depending on the orientation of the wearer, the gravimetrically low point of the chamber 204 may be at an intersection of the skin of a wearer and the fluid collection device 200 (proximate to opening 256), a corner formed in the sheath 252, or another suitable location (e.g., proximate to a region opposite the opening 256). The inlet of the conduit 108 may be positioned to be adjacent or proximate to the gravimetrically low point of the chamber 204.

During operation, a male using the fluid collection device 200 may discharge fluids (e.g., urine) into the chamber 204. The fluids may pool or otherwise be collected in the chamber 204, such as against the skin of the user (e.g., wearer). At least some of the fluids may enter the interior of the conduit 108 via the inlet of the conduit. The fluid may be drawn out of the fluid collection device 200 via the vacuum/suction provided by the vacuum source. When present and during operation, the aperture 262 may substantially maintain the pressure in the chamber 204 at atmospheric pressure even though fluid is introduced into and subsequently removed from the chamber 204.

The fluid collection devices disclosed herein are used in fluid collection systems to collect and remove fluids from a wearer of the device. As the vacuum source (FIG. 3) applies a vacuum/suction in the conduit 108, the fluid(s) in the chamber 104 or 204 (e.g., at the second end region such as in the reservoir 222) may be drawn into the inlet and out of the fluid collection device 100 or 200 via the conduit 108.

Figure 3:
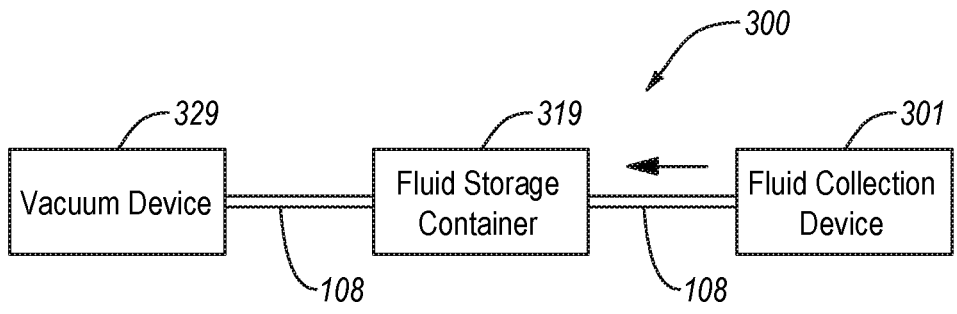
FIG. 3 is a block diagram of a system for fluid collection, according to an embodiment.

FIG. 3 is a block diagram of a system 300 for fluid collection, according to an embodiment. The system 300 includes a fluid collection device 301, a fluid storage container 319, and a vacuum source 329. The fluid collection device 301, the fluid storage container 319, and the vacuum source 329 may be fluidly coupled to each other via one or more conduits 108. For example, fluid collection device 301 may be operably coupled to one or more of the fluid storage container 319 or the (portable) vacuum source 329 via the conduits 108.

The fluid collection device 301 may be similar or identical to any of the fluid collection devices disclosed herein, such as a male or female fluid collection device. For example, the fluid collection device 301 may include a fluid impermeable barrier having an outer surface and an inner surface, where the inner surface at least partially defines a chamber within the fluid collection device 301. The fluid impermeable barrier also defines an opening configured to be positioned adjacent to a female urethra or have a male urethra positioned therethrough. The fluid impermeable barrier may be similar or identical to the any of the fluid impermeable barriers disclosed herein. The fluid collection device 301 includes a wicking material disposed within the fluid impermeable barrier, such as any of the wicking materials disclosed herein. The fluid collection device 301 may include a conduit including an inlet and an outlet as disclosed herein. The outlet may be fluidly coupled to the fluid storage container and the inlet may be positioned in a portion of the chamber selected to be at a gravimetrically low point of the fluid collection device when worn by a user. The fluid collection device 301 may an antimicrobial material carried by one or more of the fluid impermeable barrier, the wicking material, or the conduit as disclosed herein. The antimicrobial material may be an antibiotic or antifungal material, such as any of those disclosed herein. The antimicrobial material may inhibit or prevent the growth and transmission of bacteria, fungi, or other unwanted microbes when utilizing the fluid collection devices and systems disclosed herein.

Fluid (e.g., urine or other bodily fluids) collected in the fluid collection device 301 may be removed from the fluid collection device 301 via the conduit 108 which protrudes into an interior region of the fluid collection device 301. For example, a first open end of the conduit 108 may extend into the fluid collection device 301 to a reservoir therein. The second open end of the conduit 108 may extend into the fluid collection device 301 or the vacuum source 329. The suction force may be introduced into the interior region of the fluid collection device 301 via the first open end of the conduit 108 responsive to a suction (e.g., vacuum) force applied at the second end of the conduit 108. The suction force may be applied to the second open end of the conduit 108 by the vacuum source 329 either directly or indirectly.

The suction force may be applied indirectly via the fluid storage container 319. For example, the second open end (e.g., outlet) of the conduit 108 may be disposed within the fluid storage container 319 and an additional conduit 108 may extend from the fluid storage container 319 to the vacuum source 329. Accordingly, the vacuum source 329 may indirectly apply suction to the fluid collection device 301 via the fluid storage container 319. In such examples, the vacuum source 329 may provide a vacuum/suction through the fluid storage container to the fluid collection device to provide suction in the chamber of the fluid collection device. Accordingly, a vacuum (e.g., suction) may be drawn through fluid collection device 301 via the fluid storage container 319. As the fluid is drained from the chamber, the fluid may travel through the first section of conduit to the fluid storage container where it may be retained. Fluid, such as urine, may be drained from the fluid collection device 301 using the vacuum source 329.

In some examples, the suction force may be applied directly via the vacuum source 329. For example, the second open end of the conduit 108 may be disposed within the vacuum source 329. An additional conduit 108 may extend from the vacuum source 329 to a point outside of the fluid collection device 301, such as to the fluid storage container 319. In such examples, the vacuum source 329 may be disposed between the fluid collection device 301 and the fluid storage container 319. In examples, the fluid storage container 319 may include a bag (e.g., drainage bag), a bottle or cup (e.g., collection jar), or any other enclosed container for storing bodily fluids such as urine.

The vacuum source 329 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 329 may provide a vacuum or suction to remove fluid from the fluid collection device 301. In examples, the vacuum source 329 may be powered by one or more of a power cord (e.g., connected to a power socket), one or more batteries, or even manual power (e.g., a hand operated vacuum pump). The vacuum sources 329 disclosed herein may include one or more of a switch, a button, a plug, a remote, or any other device suitable to activate the vacuum source 329.

FIG. 4 is a flow diagram of a method 400 to use any of the fluid collection devices and/or fluid collection systems disclosed herein, according to an example. The method 400 may include act 410, which recites "positioning an opening of a fluid collection device adjacent to a female urethra or around a male urethra, the fluid collection device including a fluid impermeable barrier having an outer surface and an inner surface, the inner surface at least partially defining a chamber, the fluid impermeable barrier also defining an opening configured to be positioned adjacent to a female urethra or have a male urethra positioned therethrough; a wicking material disposed within the fluid impermeable barrier; a conduit including an inlet and an outlet, the outlet being fluidly coupled to a fluid storage container and the inlet being positioned in a portion of the chamber selected to be at a gravimetrically low point of the fluid collection device when worn by a user; and an antimicrobial material carried by one or more of the fluid impermeable barrier or the wicking material." Act 410 may be followed by act 420, which recites "receiving fluid from the female urethra or the male urethra into a chamber of the fluid collection device." Act 420 may be followed by act 430, which recites "applying suction with a vacuum source effective to suction the fluid from the chamber via a conduit disposed therein and fluidly coupled to the vacuum source."

Acts 410, 420, 430 of the method 400 are for illustrative purposes. For example, the act 410, 420, 430 of the method 400 may be performed in different orders, split into multiple acts, modified, supplemented, or combined. In an example, one or more of the acts 410, 420, 430 of the method 400 may be omitted from the method 400. Any of the acts 410, 420, or 430 may include using any of the fluid collection devices or systems disclosed herein.

Act 410 recites "positioning an opening of a fluid collection device adjacent to a female urethra or around a male urethra, the fluid collection device including a fluid impermeable barrier having an outer surface and an inner surface, the inner surface at least partially defining a chamber, the fluid impermeable barrier also defining an opening configured to be positioned adjacent to a female urethra or have a male urethra positioned therethrough; a wicking material disposed within the fluid impermeable barrier; a conduit including an inlet and an outlet, the outlet being fluidly coupled to a fluid storage container and the inlet being positioned in a portion of the chamber selected to be at a gravimetrically low point of the fluid collection device when worn by a user; and an antimicrobial material carried by one or more of the fluid impermeable barrier or the wicking material." The fluid collection device or components thereof may be similar or identical to any of the fluid collection devices (e.g., 100 or 200) disclosed herein, in one or more aspects.

In some examples, act 410 may include positioning the opening of a female fluid collection device such that the fluid permeable membrane of the female fluid collection device abuts or is positioned proximate to (e.g., over) the female urethra. In some examples, act 410 may include positioning a receptacle of a male fluid collection device around (e.g., over) the male urethra such that the male urethra is positioned in the receptacle. In such an example, act 410 may include positioning the sheath of the male fluid collection device in a hollowed region of the receptacle such that the male urethra is positioned through an opening of the sheath of the male fluid collection device and into the chamber of the male fluid collection device. In some examples, the act 410 may include positioning a penis within the fluid collection device, such as in the chamber thereof. In some examples, positioning an opening of a fluid collection device adjacent to a female urethra or around a male urethra may include positioning the opening over the female urethra, such as positioning a longitudinally extending opening of the fluid collection device over the female urethra.

Act 420 recites "receiving fluid from the female urethra or the male urethra into the chamber of the fluid collection device." For example, act 420 may include wicking the fluid(s) away from the opening using a fluid permeable membrane and a fluid permeable support. In some examples, act 420 may include receiving the fluid(s) into the chamber of the sheath of the male fluid collection device. In either example, act 420 may include flowing the fluid towards a portion of the chamber that is fluidly coupled to an inlet of a conduit, which may be in fluid communication a vacuum source. For instance, act 420 may include flowing the fluid(s) to a substantially unoccupied portion of the chamber (e.g., a reservoir), to a gravimetrically low point of the chamber, etc. In some examples, receiving fluid(s) from the female urethra or the male urethra into a chamber of the fluid collection device may include wicking the fluid (e.g., urine) into the chamber via the fluid permeable membrane and fluid permeable support of the fluid collection device. For example, wicking the fluid into the chamber via the fluid permeable membrane and fluid permeable support may include wicking urine into a reservoir in the fluid collection device.

Act 430 recites, "applying suction with a vacuum source effective to suction the fluid(s) from the chamber via a conduit disposed therein and fluidly coupled to the vacuum source." In some examples, applying suction with a vacuum source effective to suction the fluid(s) from the chamber via a conduit disposed therein and fluidly coupled to the vacuum source may include using any of the vacuum sources disclosed herein. In an example, act 430 may include activating the vacuum source (e.g., suction device) in fluid communication with the inlet of the conduit in the fluid collection device. In some examples, activating the vacuum source in fluid communication with the inlet of the conduit in the fluid collection device may include supplying power to the vacuum source by one or more of flipping an on/off switch, pressing a button, plugging the vacuum source into a power outlet, putting batteries into the vacuum source, etc. In some examples, the vacuum source may include a hand operated vacuum pump and applying suction with a vacuum source may include manually operating the hand operated vacuum pump effective to suction the fluid(s) from the chamber via the conduit disposed therein that is fluidly coupled to the vacuum source.

In some examples, applying suction with a vacuum source effective to suction the fluid(s) from the chamber via a conduit disposed therein and fluidly coupled to the vacuum source may be effective to remove at least some fluid (e.g., urine) from the chamber (e.g., interior region) of the fluid collection device. In some examples, applying suction with a vacuum source effective to suction the fluid(s) from the chamber via a conduit disposed therein and fluidly coupled to the vacuum source may be effective to transfer at least some of the fluid from the chamber of the fluid collection device to a fluid storage container (e.g., a bottle or bag). In some examples, applying suction with a vacuum source effective to suction the fluid(s) from the chamber may include removing fluid from one or more of a reservoir, fluid permeable support, or fluid permeable membrane of the fluid collection device.

In some examples, the vacuum source (e.g., suction device) may be disposed on or within the fluid collection device. In some examples, the vacuum source may be spaced from the fluid collection device.

In some examples, applying suction with a vacuum source effective to suction the fluid(s) from the chamber via a conduit disposed therein and fluidly coupled to the vacuum source may include detecting moisture in the chamber (e.g., via one or more moisture sensors) and responsive thereto, activating the vacuum source to provide suction in the chamber. The control of the vacuum source responsive to the signals indicating that moisture or a level thereof is present in the chamber may be automatic, such as via a controller (e.g., computer programmed to perform the operation), or may merely provide an indication that a level of moisture is present that may necessitate removal of fluid from the chamber of the fluid collection device. In the latter case, a user may receive the indication (e.g., from the controller) and activate the vacuum pump manually.

In an example, the method 400 may include collecting the fluid(s) that are removed from the fluid collection device, such as into a fluid storage container that is spaced from the fluid collection device and fluidly coupled to the conduit. The fluid storage container may include any of the fluid storage containers disclosed herein.

As used herein, the term "about" or "substantially" refers to an allowable variance of the term modified by "about" by ±10% or ±5%. Further, the terms "less than," "or less," "greater than", "more than," or "or more" include as an endpoint, the value that is modified by the terms "less than," "or less," "greater than," "more than," or "or more."

While various aspects and embodiments have been disclosed herein, other aspects and embodiments are contemplated. The various aspects and embodiment disclosed herein are for purposes of illustration and are not intended to be limiting.

What is claimed is:

1. A fluid collection device, comprising:
a fluid impermeable barrier having an outer surface and an inner surface, the inner surface at least partially defining a chamber, the fluid impermeable barrier also defining an opening extending therethrough, the opening is configured to be positioned adjacent to a female urethra or a male urethra;
a fluid permeable material disposed at least partially in the chamber and positioned to contact skin of a wearer through the opening, the fluid permeable material including:
  a fluid permeable membrane disposed at least partially within the chamber and having an outer surface extending across the opening; and
  a fluid permeable support disposed at least partially within the chamber and positioned to support the fluid permeable membrane;
an antimicrobial material carried by the fluid permeable material and the fluid impermeable barrier, wherein the antimicrobial material is disposed only on the outer surface of the fluid impermeable barrier and the outer surface of the fluid permeable membrane that are expected to be in contact with a wearer when in use.

2. The fluid collection device of claim 1, wherein the antimicrobial material includes one or more of an antibiotic material or an antifungal material.

3. The fluid collection device of claim 1, wherein the antimicrobial material includes one or more of an organic compound, a polymeric biocide, silver, copper, or aluminum.

4. The fluid collection device of claim 1, wherein the antimicrobial material is disposed on the inner surface.

5. The fluid collection device of claim 1, wherein the antimicrobial material is incorporated into a material of the fluid impermeable barrier.

6. The fluid collection device of claim 1, wherein:
the antimicrobial material includes one or more of a polymeric biocide, silver, copper, or aluminum; and
one or both of the fluid permeable membrane or fluid permeable support include fibers incorporating the antimicrobial material.

7. The fluid collection device of claim 1, further comprising a conduit including an inlet and an outlet, the inlet being positioned within the fluid collection device and the outlet is configured to be fluidly coupled to a fluid storage container.

8. The fluid collection device of claim 7, wherein:
the fluid impermeable barrier and one or more of the fluid permeable membrane or fluid permeable support define a reservoir therebetween; and
the inlet is disposed in the reservoir.

\*    \*    \*    \*    \*